(12) United States Patent
Hong et al.

(10) Patent No.: US 9,901,659 B2
(45) Date of Patent: Feb. 27, 2018

(54) WET-ELECTROSPUN BIODEGRADABLE SCAFFOLD AND USES THEREFOR

(75) Inventors: Yi Hong, Pittsburgh, PA (US); Nicholas J. Amoroso, Pittsburgh, PA (US); Kazuro Lee Fujimoto, Pittsburgh, PA (US); Ryotaro Hashizume, Pittsburgh, PA (US); William R. Wagner, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 615 days.

(21) Appl. No.: 13/698,757

(22) PCT Filed: May 27, 2011

(86) PCT No.: PCT/US2011/038332
§ 371 (c)(1),
(2), (4) Date: Apr. 2, 2014

(87) PCT Pub. No.: WO2011/150328
PCT Pub. Date: Dec. 1, 2011

(65) Prior Publication Data
US 2014/0377213 A1     Dec. 25, 2014

Related U.S. Application Data

(60) Provisional application No. 61/349,031, filed on May 27, 2010.

(51) Int. Cl.
*A61L 27/36*     (2006.01)
*A61L 27/58*     (2006.01)
(Continued)

(52) U.S. Cl.
CPC ........... *A61L 27/3616* (2013.01); *A61L 27/18* (2013.01); *A61L 27/3691* (2013.01); *A61L 27/54* (2013.01);
(Continued)

(58) Field of Classification Search
CPC .. A61L 27/18; A61L 27/3616; A61L 27/3691; A61L 27/54; A61L 27/58; C12N 2533/30; C12N 5/0068
See application file for complete search history.

(56) References Cited

U.S. PATENT DOCUMENTS

| 4,902,508 A | 2/1990 | Badylak et al. |
| 4,956,178 A | 9/1990 | Badylak et al. |

(Continued)

FOREIGN PATENT DOCUMENTS

| WO | 2008024640 A2 | 2/2008 | |
| WO | WO 2008024640 A2 * | 2/2008 | ......... A61L 27/3843 |

OTHER PUBLICATIONS

Seifalian et al., "In vivo biostability of a poly(carbonate-urea)urethane graft", 2003, Biomaterials, vol. 24, pp. 2549-2557.*
(Continued)

*Primary Examiner* — Michael B. Pallay
(74) *Attorney, Agent, or Firm* — The Webb Law Firm

(57) ABSTRACT

A cell growth matrix is provided that comprises a biodegradable elastomeric polymer electrodeposited concurrently with a sprayed or electrosprayed liquid that is a physiological solution or which comprises a mammalian blood product such as serum, plasma or platelet rich plasma. The matrix is useful as a cell-growth matrix and for repair of a tissue in a mammal, for instance by implantation in a mammal at a site in need of repair, such as in an abdominal wall.

21 Claims, 14 Drawing Sheets

(51) Int. Cl.
  *A61L 27/18* (2006.01)
  *A61L 27/54* (2006.01)
  *C12N 5/00* (2006.01)
(52) U.S. Cl.
  CPC ............ *A61L 27/58* (2013.01); *C12N 5/0068* (2013.01); *C12N 2533/30* (2013.01)

(56) References Cited

U.S. PATENT DOCUMENTS

| | | | |
|---|---|---|---|
| 5,171,262 | A | 12/1992 | MacGregor |
| 5,275,826 | A | 1/1994 | Badylak et al. |
| 5,281,422 | A | 1/1994 | Badylak et al. |
| 5,352,463 | A | 10/1994 | Badylak et al. |
| 5,372,821 | A | 12/1994 | Badylak et al. |
| 5,516,533 | A | 5/1996 | Benson |
| 5,554,389 | A | 9/1996 | Badylak et al. |
| 5,573,784 | A | 11/1996 | Badylak et al. |
| 5,645,860 | A | 7/1997 | Knapp, Jr. et al. |
| 5,711,969 | A | 1/1998 | Patel et al. |
| 5,753,267 | A | 5/1998 | Badylak et al. |
| 5,762,966 | A | 6/1998 | Knapp, Jr. et al. |
| 5,866,414 | A | 2/1999 | Badylak et al. |
| 6,099,567 | A | 8/2000 | Badylak et al. |
| 6,485,723 | B1 | 11/2002 | Badylak et al. |
| 6,554,857 | B1 | 4/2003 | Zilla et al. |
| 6,576,265 | B1 | 6/2003 | Spievack |
| 6,579,538 | B1 | 6/2003 | Spievack |
| 6,696,270 | B2 | 2/2004 | Badylak et al. |
| 6,783,776 | B2 | 8/2004 | Spievack |
| 6,793,939 | B2 | 9/2004 | Badylak |
| 6,849,273 | B2 | 2/2005 | Spievack |
| 6,852,339 | B2 | 2/2005 | Spievack |
| 6,861,074 | B2 | 3/2005 | Spievack |
| 6,887,495 | B2 | 5/2005 | Spievack |
| 6,890,562 | B2 | 5/2005 | Spievack |
| 6,890,563 | B2 | 5/2005 | Spievack |
| 6,890,564 | B2 | 5/2005 | Spievack |
| 6,893,666 | B2 | 5/2005 | Spievack |
| 7,235,295 | B2 | 6/2007 | Laurencin et al. |
| 7,374,774 | B2 | 5/2008 | Bowlin et al. |
| 8,267,960 | B2 | 9/2012 | Argenta et al. |
| 2002/0081732 | A1 | 6/2002 | Bowlin et al. |
| 2002/0090725 | A1 | 7/2002 | Simpson et al. |
| 2003/0100944 | A1 | 5/2003 | Laksin et al. |
| 2006/0257377 | A1 | 11/2006 | Atala et al. |
| 2007/0014755 | A1 | 1/2007 | Beckman et al. |
| 2007/0207186 | A1 | 9/2007 | Scanlon et al. |
| 2007/0225631 | A1 | 9/2007 | Bowlin et al. |
| 2007/0275458 | A1 | 11/2007 | Gouma |
| 2008/0009830 | A1 | 1/2008 | Fujimoto et al. |
| 2008/0096975 | A1 | 4/2008 | Guan et al. |
| 2008/0159985 | A1 | 7/2008 | Bowlin et al. |
| 2008/0208323 | A1 | 8/2008 | El-Kurdi et al. |
| 2008/0260831 | A1 | 10/2008 | Badylak et al. |
| 2008/0268019 | A1 | 10/2008 | Badylak et al. |
| 2009/0069903 | A1* | 3/2009 | Shortkoff ............... A61L 27/24 623/23.72 |
| 2010/0040584 | A1* | 2/2010 | Melero-Martin ...... A61K 35/28 424/93.7 |
| 2011/0015760 | A1* | 1/2011 | Kullas ................... A61F 2/0063 623/23.72 |

OTHER PUBLICATIONS

Badylak et al., "Esophageal Reconstruction with ECM and Muscle Tissue in a Dog Model," Journal of Surgical Research, 2005, pp. 87-97, vol. 128
Badylak et al., "Resorbable bioscaffold for esophageal repair in a dog model," Journal of Pediatric Surgery, Jul. 2000, pp. 1097-1103, vol. 35, No. 7.
Badylak, "The Extracellular Matrix as a Scaffold for Tissue Reconstruction," Seminars in Cell & Developmenal Biology, 2002, pp. 377-383, vol. 13.
Badylak, "Xenogeneic extracellular matrix as a scaffold for tissue reconstruction," Transplant Immunology, Apr. 2004, pp. 367-377, vol. 12.
Becker et al., "AlloDerm versus DermaMatrix in Immediate Expander-Based Breast Reconstruction: A preliminary Comparison of Complication Profiles and Material Compliance," Plastic and Reconstructive Surgery, Jan. 2009, pp. 1-6, vol. 123, No. 1.
Bellon et al., "Peritoneal Effects of Prosthetic Meshes Used to Repair Abdominal Wall Defects: Monitoring Adhesions by Sequential Laparoscopy," Journal of Laparoendoscopic & Advanced Surgical Techniques, 2007, pp. 160-167, vol. 17, No. 2.
Bernacca et al., "Polyurethane heart valve durability: effects of leaflet thickness and material," The International Journal of Artifical Organs, 1997, pp. 327-331, vol. 20, No. 6.
Billiar et al., "Biaxial Mechanical Properties of the Natural and Glutaraldehyde Treated Aortic Valve Cusp—Part I: Experimental Results," Journal of Biomechanical Engineering, Feb. 2000, pp. 23-30. vol. 122.
Bir et al., "Angiogenic properties of sustained release platelet-rich plasma: Characterization in-vitro and in the ischemic hind limb of the mouse," Journal of Vascular Surgery, Oct. 2009, pp. 870-879.e2, vol. 50, No. 4.
Brightman et al., "Time-Lapse Confocal Reflection Microscopy of Collagen Fibrillogenesis and Extracellular Matrix Assembly in Vitro," Biopolymers, 2000, pp. 222-234, vol. 54.
Chaudhuri et al., "Detection and gradation of oriented texture," Pattern Recognition Letters, Feb. 1993, pp. 147-153, vol. 14.
Courtney et al., "Analysis and design of novel electrospun PEUU scaffolds for soft tissue engineering," ASME 2005 Summer Bioengineering Conference, Vail, CO, Jun. 22-26, 2005, Published on CD, Proceedings of the 2005 Summer Bioengineering Conference, Vail Cascade REsort and Spa, Vail, CO; Abstract #b0241329.
Courtney et al., "Analysis and Design of novel electrospun PEUU scaffolds for Soft Tissue Engineering," The 8th Annual Meeting of the Tissue Engineering Society International, Oct. 22-25, 2005, Shanghai, P.R. China. Published on CD, Final Program and Abstract Book TESI 2005, Abstract #193.
Courtney et al., "Design and analysis of tissue engineering scaffolds that mimic soft tissue mechanical anisotropy," Biomaterials, 2006, pp. 3631-3638, vol. 27.
Courtney et al., "Incorporation of fiber tortuosity effects in a constitutive model for electrospun scaffolds," ASME 2006 Summer Bioengineering Conference, Jun. 21-25, 2005, Amelia Island, FL. Published on CD, Proceedings of the 2006 Summer Bioengineering Conference, Abstract #BIO2005-157686.
Courtney et al. "Meso- and Micromechanics of Elastomeric Electrospun PEUU Scaffolds for Cardiovascular Tissue Engineering," Regenerate World Congress on Tissue Engineering and Regnerative Medicine, Apr. 25-27, 2006, Pittsburgh, PA, Published on CD: Conference Proceedings Regenerate World Congress on Tissue Engineering and Regenerative Medicine, Abstract #572.
Courtney et al., "Micromechanics of Electrospun Poly Ester Urethane Urea Scaffolds," Society for Biomaterials 2006 Annual Meeting, Apr. 26, 2009, 2006, Pittsburgh, PA. Published on CD, Transactions of the Annual Meeting of the Society for Biomaterials, vol. XXIX, Abstract #163.
Courtney et al., "Micromechanics of electrospun poly ester urethane urea scaffolds for soft tissue engineering," Journal of Biomechanics, Oral Presentations, 2006, p. S262, vol. 39. Supplement 1.
Courtney et al., "Poly(ester urethane) Urea Elastomeric Scaffolds for Soft Tissue Engineering," Society for Biomaterials 30th Annual Meeting, Memphis, TN, Apr. 27-30, 2005. Published on CD, Transactions of the 30th Annual Meeting.
D'Addario et al., "h-Caldesmon as a specific marker of smooth muscle cell differentiation in some soft tissue tumors of the skin," Journal of Cutaneous Pathology, 2002, pp. 426-429, vol. 29.
Deglau et al., "Surface modification of vascular tissue for targeted delivery of endothelial cells and microspheres," Annals of Biomedical Engineering; The Journal of the Biomedical Engineering Society, Oct. 12-14, 2000, p. S-23.

(56) References Cited

OTHER PUBLICATIONS

Dubay et al., "Mesh incisional herniorrhaphy increases abdominal wall elastic properties: A mechanism for decreased hernia recurrences in comparison with suture repairs," Surgery, Jul. 2006, pp. 14-24, vol. 140, No. 1.

Dubay et al., "Progressive fascial wound failure impairs subsequent abdominal wall repairs: A new animal model of incisional hernia formation," Surgery, Apr. 2005, pp. 463-471, vol. 137, No. 4.

El-Kurdi et al., "Transient elastic support for vein grafts using a constricting microfibrillar polymer wrap," Biomaterials, 2008, pp. 3213-3220, vol. 29.

Fujimoto et al., "An Elastic, Biodegradable Cardiac Patch Induces Contractile Smooth Muscle and Improves Cardiac Remodeling and Function in Subacute Myocardial Infarction," Journal of the American College of Cardiology, Jun. 12, 2007, pp. 2292-2300, vol. 49, No. 23.

Grashow et al., "Biaxial Stress-Stretch Behavior of the Mitral Valve Anterior Leaflet at Physiologic Strain Rates," Annals of Biomedical Engineering, Feb. 2006, pp. 315-325, vol. 34, No. 2.

Guan et al., "Biodegradable poly(ether ester urethane)urea elastomers based on poly(ether ester) triblock copolymers and putrescine: synthesis, characterization and cytocompatibility," Biomaterials, 2004, pp. 85-96, vol. 25.

Guan et al., "Preparation and characterization of highly porous, biodegradable polyurethane scaffolds for soft tissue applications," Biomaterials, 2005, pp. 3961-3971, vol. 26.

Guan et al., "Synthesis, characterization and cytocompatibility of elastomeric, biodegradable poly(ester-urethane) ureas based on poly(caprolactone) and putrescine," J Biomed Mater Res., Sep. 5, 2002, pp. 493-503, vol. 61, No. 3.

Guan et al., "Synthesis, Characterization and Cytocompatibility of Polyurethaneurea Elastomers with Designed Elastase Sensitivity," Biomacromolecules, 2005, pp. 2833-2842, vol. 6.

Hashizume et al., "Morphological and mechanical characteristics of the reconstructed rat abdominal wall following use of a wet electrospun biodegradable polyurethane elastomer scaffold," Biomaterials, 2010, pp. 3253-3265, vol. 31.

Hong et al., "Generating Elastic, Biodegradable Polyurethane/Poly(lactide-co-glycolide) Fibrous Sheets with Controlled Antibiotic Release via Two-Stream Electrospinning," Biomacromolecules, 2008, pp. 1200-1207, vol. 9.

Hong et al., "Tailoring the degradation kinetics of poly(ester carbonate urethane)urea thermoplastic elastomers for tissue engineering scaffolds," Biomaterials, 2010, pp. 4249-4258, vol. 31.

Karlon et al., "Automated Measurement of Myofiber Disarray in Transgenic Mice with Ventricular Expression of ras," The Anatomical Record, 1998, pp. 612-625, vol. 252.

Lai et al., "Peritoneal Regeneration Induced by an Acellular Bovine Pericardial Patch in the Repair of Abdominal Wall Defects," Journal of Surgical Research, 2005, pp. 85-92, vol. 127.

Lee et al., "Nanofiber alignment and direction of mechanical strain affect the ECM production of human ACL fibroblast," Biomaterials, 2005, pp. 1261-1270, vol. 26.

Matsuda et al., "Mechano-active scaffold design of small-diameter artificial graft made of electrospun segmented polyurethane fabrics," Journal of Biomedical Materials Research A, Apr. 1, 2005, pp. 125-131, vol. 73A, No. 1.

Middleton et al., "Synthetic Biodegradable Polymers as Medical Devices," Medical Plastics and Biomaterials Magazine, Mar. 1998, 10 pages.

Natale et al., "Pelvic floor reconstructive surgery: which aspects remain controversial?," Current Opinions in Urology, 2006, pp. 407-412, vol. 16.

Nedovic et al., "Cell immobilisation by electrostatic droplet generation," Landbauforschung Volkenrode, 2002, pp. 11-17. vol. SH 241.

Radisic et al., "Medium perfusion enables engineering of compact and contractile cardiac tissue," Am J Physiol Heart Circ Physiol, 2004, pp. H507-H516, vol. 286.

Riboldi et al., "Electrospun degradable polyesterurethane membranes: potential scaffolds for skeletal muscle tissue engineering," Biomaterials, 2005, pp. 4606-4615, vol. 26.

Sacks et al., "Analysis and design of novel electrospun PEUU scaffolds for soft tissue engineering," MRS 2005 Fall, Boston, MA, Nov. 30, 2005, Session L13.1.

Sacks, "Biaxial Mechanical Evaluation of Planar Biological Materials," Journal of Elasticity, 2000, pp. 199-246, vol. 61.

Sampson et al., "Platelet rich plasma injection grafts for musculoskeletal injuries: a review," Curr Rev Musculoskelet Med, 2008, 10 pages.

Santucci et al., "Resorbable Extracellular Matrix Grafts in Urologic Reconstruction," International Braz J Urol; Official Journal of the Brazilian Society of Urology, May-Jun. 2005, pp. 192-203, vol. 31, No. 3.

Sell et al., "Electrospinning of collagen/biopolymers for regenerative medicine and cardiovascular tissue engineering," Advanced Drug Delivery Reviews, 2009, pp. 1007-1019, vol. 61.

Sergent et al., "Mechanical evaluation of synthetic biomaterials used in the correction of pelvic floor disorders—Experimental study in rabbits," European Journal of Obstetrics & Gynecology and Reproductive Biology, 2009, pp. 106-110, vol. 147.

Stankus et al., "Fabrication of biodegradable elastomeric scaffolds with sub-micron morphologies," Journal of Biomedical Materials Research A, Sep. 15, 2004, pp. 603-614, vol. 70A, No. 4.

Stankus et al., "Fabrication of cell microintegrated blood vessel constructs through electrohydrodynamic atomization," Biomaterials, 2007, pp. 2738-2746, vol. 28.

Stankus et al., "Hybrid nanofibrous scaffolds from electrospinning of a synthetic biodegradable elastomer and urinary bladder matrix," J. Biomater. Sci. Polymer Edn, 2008, pp. 635-652, vol. 19, No. 5.

Stankus et al., "Microintegrating smooth muscle cells into a biodegradable, elastomeric fiber matrix," Biomaterials, 2006, pp. 735-744, vol. 27.

Stella et al., "Tissue-to-cellular level deformation coupling in cell micro-integrated elastomeric scaffolds," Biomaterials, 2008, pp. 3228-3236, vol. 29.

Temple et al., "Electrostatic transportation of living cells through air," Abstracts of Papers, 223 ACS National Meeting, Orlando, FL, Apr. 7-11, 2002.

Veazey et al., Mammalian Cell Delivery via Aerosol Deposition, Journal of Biomedical Materials Research B: Applied Biomaterials, Feb. 15, 2005, pp. 334-338, vol. 72B, No. 2.

Venere, "New materials hold promise for human healing applications," Purdue News, Mar. 22, 2001, 4 pages.

Wright Medical Technology, "Comparative analysis: Graftjacket Periosteum Replacement Scaffold & SIS Porcine Small Intestinal Submucosa," Copyright 2002, 6 pages.

Xu et al., "Aligned biodegradable nanofibrous structure: a potential scaffold for blood vessel engineering," Biomaterials, 2004, pp. 877-886, vol. 25.

Yokoyama et al., "Novel wet electrospinning system for fabrication of spongiform nanofiber 3-dimensional fabric," Materials Letters, 2009, pp. 754-756, vol. 63.

* cited by examiner

WET-ELECTROSPUN BIODEGRADABLE SCAFFOLD AND USES THEREFOR

CROSS REFERENCE TO RELATED APPLICATIONS

This application is a National Stage of International Patent Application No. PCT/US2011/038332, filed May 27, 2011, which claims the benefit of U.S. Provisional Patent Application No. 61/349,031, filed May 27, 2010, each of which is herein incorporated by reference in its entirety.

STATEMENT REGARDING FEDERAL FUNDING

This invention was made with government support under Grant No. W81XWH-08-2-0032 awarded by the Armed Forces Institute for Regenerative Medicine, and Grant No. R01 HL-068816 awarded by the National Institutes of Health. The government has certain rights in the invention.

Employing prosthetic materials in abdominal wall repair is commonplace, with clear benefits over repair by direct tissue apposition for larger defects. Synthetic, non-biodegradable biomaterials such as polypropylene and polyester meshes, as well as expanded polytetrafluoroethylene (ePTFE) are widely employed for this purpose with few complications. Complications associated with placement of these materials, although not commonly encountered, include seromas and fistulas, chronic patient discomfort, surgical site infections and decreasing abdominal wall compliance that can infringe upon the patient's physical activity. These complications are generally more common in the settings of massive ventral hernia, contaminated fields, and emergency surgery. An array of biologic prosthetic materials from both allogenic and xenogenic tissue sources, processed with and without chemical crosslinking, have been utilized in an effort to address some of the limits associated with synthetic materials. The potential benefits of biologic materials include improved infection resistance, host tissue ingrowth, and less adhesion formation. However, the downsides of these materials include concerns with mechanical failure, higher costs, and greater difficulty in tailoring physical properties, which can lead to mechanical property mismatch at the native tissue interface with the implant.

SUMMARY

Although a variety of materials are currently used for abdominal wall repair, general complications encountered include herniation, infection, and mechanical mismatch with native tissue. An approach wherein a degradable synthetic material is ultimately replaced by tissue mechanically approximating the native state could obviate these complications. Provided herein are matrices comprising a biodegradable elastomeric polymer electrodeposited concurrently with an electrosprayed liquid comprising either a mammalian blood product, such as serum, plasma or platelet rich plasma or a physiological solution, such as water, normal (NS, e.g., 0.9% wt.) saline or phosphate-buffered saline (PBS). The biodegradable elastomeric polymer is poly(ester urethane)urea (PEUU), poly(ether ester urethane)urea (PEEUU), poly(ester carbonate)urethane urea (PECUU) or poly(carbonate)urethane urea (PCUU) in certain embodiments. These matrices show superior cellular infiltration as compared to similar materials that are dry-electrodeposited or other materials, such as expanded polytetrafluoroethylene (ePTFE). These matrices can be used for any tissue repair or reconstruction by implanting the matrix at a site in a patient in need of repair, including, without limitation: skin, blood vessel(s), muscle, esophagus, trachea, stomach, intestine, rectum or bladder.

Thus, a method of repairing a defect in a tissue, such as an abdominal wall or heart of a mammal, such as a human, but including any mammal, such as a dog, cat, horse, etc. is provided. The method comprises implanting a matrix of a wet-electrodeposited biodegradable, elastomeric polymer, such as poly(ester urethane) urea (PEUU), poly(ether ester urethane)urea (PEEUU), poly(ester carbonate)urethane urea (PECUU) and poly(carbonate)urethane urea (PCUU) nonwoven matrix in a mammal. The matrix is electrodeposited as it is electrosprayed with either a blood product-containing liquid, such as a serum-, plasma- or platelet rich plasma-containing liquid or a physiological solution, such as water, NS or PBS. Also provided is method of growing cells (in vitro or in vivo). The method comprises contacting cells with a matrix of a wet-electrodeposited biodegradable, elastomeric polymer, such as poly(ester urethane) urea (PEUU), poly(ether ester urethane)urea (PEEUU), poly(ester carbonate)urethane urea (PECUU) and poly(carbonate)urethane urea (PCUU) nonwoven matrix. The matrix is electrodeposited as it is electrosprayed with a blood product-containing liquid, such as a serum-, plasma- or platelet rich plasma-containing liquid.

A method of making a matrix useful, e.g., as a cell growth matrix for muscle repair, such as for repair of a defect in an abdominal wall of a mammal, is provided which comprises wet electrodepositing a biodegradable, elastomeric polymer concurrently with electrospraying a blood product-containing liquid, such as a serum-, plasma- or platelet rich plasma-containing liquid, onto the electrodeposited polymer to produce a wet-electrodeposited matrix. The polymer may be a as poly(ester urethane) urea (PEUU), poly(ether ester urethane)urea (PEEUU), poly(ester carbonate)urethane urea (PECUU) and poly(carbonate)urethane urea (PCUU) matrix. In all embodiments of the methods and matrices described herein, the matrix may be isotropic or anisotropic and is a non-woven. Also provided is a use of a nonwoven matrix comprising a biodegradable elastomeric polymer electrodeposited concurrently with a sprayed or electrosprayed liquid comprising a mammalian blood product in the manufacture of a cell growth matrix, where the biodegradable elastomeric polymer and the sprayed or electrosprayed liquid are any biodegradable elastomeric polymer and sprayed or electrosprayed liquid as described herein, for example in relation to the methods described above.

DETAILED DESCRIPTION

Figure 1:
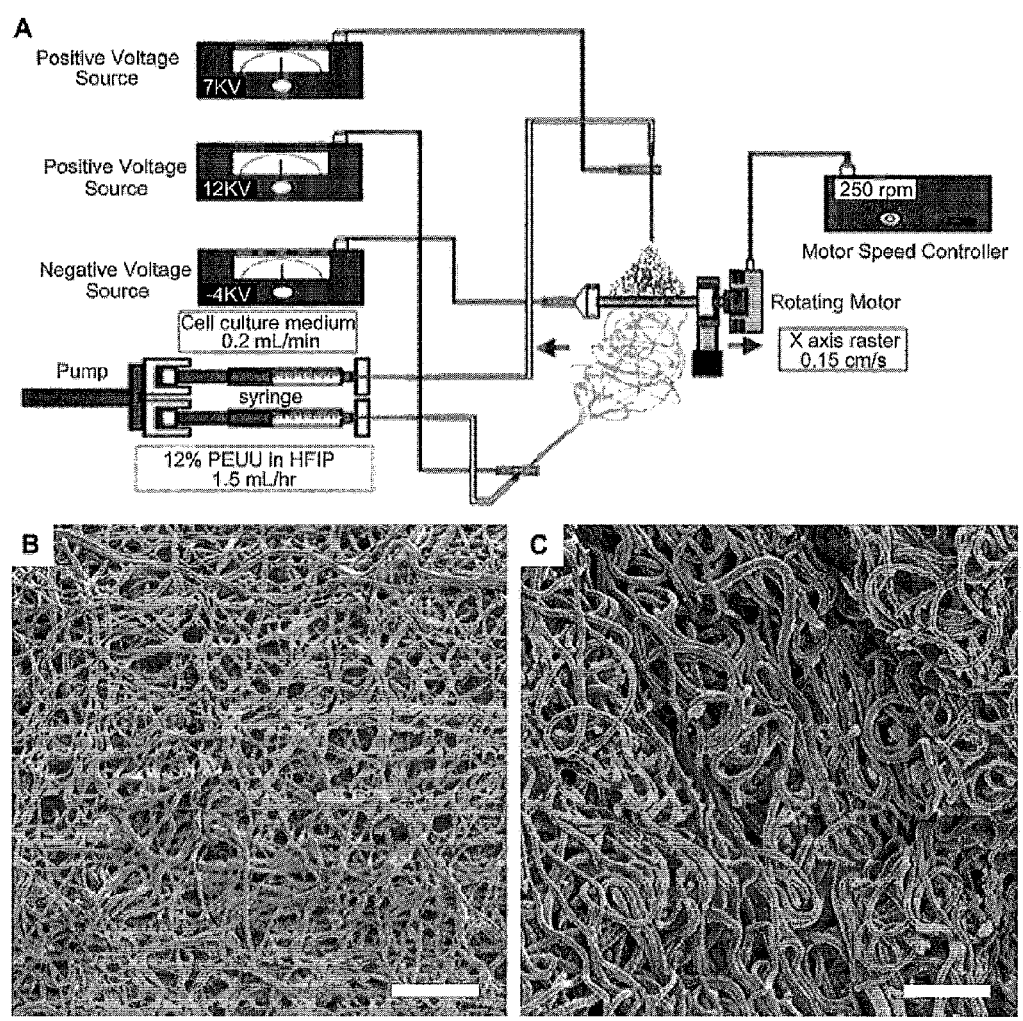
FIG. 1. Schematic of wet electrospinning where PEUU is electrospun with concurrent electrospraying of cell culture medium (A). Electron micrographs of dry ePEUU (B) and wet ePEUU (C). Scale bar: 20 μm.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

A method of repairing a defect in a tissue and a method of growing tissue are provided. The methods can be used for repairing a defect in a tissue, such as an abdominal wall or heart, of a mammal, such as a human, but including any mammal, such as a dog, cat, horse, etc. is provided. The method comprises implanting a wet-electrodeposited biodegradable elastomeric polymer, such as a as poly(ester urethane) urea (PEW), poly(ether ester urethane)urea (PEEUU), poly(ester carbonate)urethane urea (PECUU) and poly(carbonate)urethane urea (PCUU) in a mammal, typically, but not exclusively at a site in need of repair. A method of making an implantable matrix useful, e.g., for repair of a defect in an abdominal wall of a mammal is provided which comprises wet electrospinning a biodegradable polymer, such as a as poly(ester urethane) urea (PEW), poly(ether ester urethane)urea (PEEUU), poly(ester carbonate)urethane urea (PECUU) and poly(carbonate)urethane urea (PCUU), nonwoven matrix in the presence of a sprayed or electrosprayed liquid comprising serum. The nonwoven matrix described above and throughout may be used in the manufacture of a cell growth matrix. In all instances, unless otherwise specified, the serum can be xenogeneic, allogeneic, syngeneic or autogenic to the mammal.

Also described herein are methods of making an implantable matrix for muscle repair, comprising electrodepositing a biodegradable elastomeric polymer and concurrently electrospraying a liquid comprising a mammalian blood product onto the electrodeposited polymer. The biodegradable elastomeric polymer and liquid comprising a mammalian blood product may be any biodegradable elastomeric polymer and liquid comprising a mammalian blood described herein.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

A biodegradable polymer is "biocompatible" in that the polymer and degradation products thereof are substantially non-toxic to cells or organisms, including non-carcinogenic and non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

As described herein, a "fiber" an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize mechanical conditioning of the tissue. For instance, in the case of abdominal wall repair, it is desirable that the matrix dissolves over at least a week and preferably longer. More importantly, the matrix would have to retain its supportive capacity until tissue remodeling occurs, such as for at least 2-8 weeks, or longer.

A number of biocompatible, biodegradable elastomeric (co)polymers are known and have been established as useful in preparing cell growth matrices, including biodegradable poly(ester urethane) urea (PEUU), poly(ether ester urethane) urea (PEEUU), poly(ester carbonate)urethane urea (PECUU) and poly(carbonate)urethane urea (PCUU). In general, useful copolymers comprise monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

In one example, as described in US Patent Publication No. 20080268019, incorporated herein by reference for its technical disclosure, the polymer composition comprises a synthetic polymeric component and a biological polymeric component. The synthetic polymeric component may comprise a thermoplastic biodegradable elastomer, and/or the biological polymeric component may comprise an extracellular matrix-derived material. The synthetic polymeric component may comprise one or both of a poly(ester urethane) urea elastomer and a poly(ether ester urethane urea) elastomer. The elastomer may comprise a diamine, such as putrescine or lysine ethyl ester, or a diol. The elastomer may comprise a polycaprolactone or a polycaprolactone diol, such as a triblock copolymer comprising polycaprolactone or a polycaprolactone-b-polyethylene glycol-b-polycaprolactone triblock copolymer. The elastomer can be functionalized with an adhesion-promoting peptide, such as the oligopeptide RGD. In one non-limiting embodiment, the elastomer comprises an isocyanate derivative, a polycaprolactone diol, and a diamine chain extender, which may comprise a ratio of isocyanate derivative:polycaprolactone diol:diamine chain extender of about 2:1:1. In another non-limiting embodiment, the elastomer comprises an isocyanate derivative, a triblock copolymer comprising polycaprolactone, and a diamine chain extender in which the ratio of isocyanate derivative:triblock copolymer:diamine chain extender optionally is about 2:1:1. For example, as described in the Examples below, the molar feed ratio for preparation of PEUU was polycaprolactone:diisocyanatobutane:putrescine=1:2:1, and the molar feed ratio for synthesis of PEEUU, polycaprolactone-PEG-polycaprolactone copolymer:diisocyanatobutane:putrescine=1:2:1.

Other useful copolymers include: polylactide, polyglycolide, poly(lactide-co-glycolide), polycaprolactone, poly(lactide-co-caprolactone), poly(trimethylene carbonate) based polymers, polyhydroxybutyrate and its copolymer, polydioxanone, poly(ester carbonate urethane) urea, poly(carbonate urethane) urea, polycarbonate urethane, or polyester urethane. In another embodiment, natural polymers are included in the polymer composition, including gelatin, collagen, chitosan, hyaluronic acid, etc.

According to a non-limiting embodiment, the polymer composition comprises one or both of a collagen and an elastin. Collagen is a common ECM component and typically is degraded in vivo at a rate faster than many synthetic bioerodable polymers. Therefore, manipulation of collagen content in the polymer composition can be used as a method of modifying bierosion rates in vivo. Collagen may be present in the polymer composition in any useful range, including, without limitation, from about 2% wt. to about 95% wt., but more typically in the range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Use of elastin can permit slight circumferential expansion of the restrictive matrix in order to assist the tubular tissue, such as a vein, adapt to its new function, such as an arterial use. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting embodiment, collagen and elastin are present in approximately equal amounts in the polymer composition, In another embodiment, the sum of the collagen and elastin content in the polymer composition is in any useful range, including, without limitation, from about 2% wt. to about 95% wt., but more typically in the range of from about 25% wt. to about 75% wt., inclusive of all ranges and points therebetween, including from about 40% wt. to about 75% wt., including about 75% wt. and about 42.3% wt.

The biological polymeric component is useful for promoting cell growth on the elastomeric scaffold, extracting appropriate host cells for construction, remodeling, and/or enhancement of biocompatibility. In one non-limiting embodiment, the biological polymeric component comprises and includes an extracellular matrix-derived material. As used herein, the terms "extracellular matrix" and "ECM" refer to a complex mixture of structural and functional biomolecules and/or biomacromolecules including, but not limited to, structural proteins, specialized proteins, proteoglycans, glycosaminoglycans, and growth factors that surround and support cells within mammalian tissues.

Generally, any type of extracellular matrix (ECM) can be used to prepare the biological, ECM-derived polymeric component of the biodegradable elastomeric scaffold (for example and without limitation, see U.S. Pat. Nos. 4,902, 508; 4,956,178; 5,281,422; 5,352,463; 5,372,821; 5,554, 389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety for its technical disclosure). By "ECM-derived material" it is meant a composition that is prepared from a natural ECM or from an in vitro source wherein the ECM is produced by cultured cells and comprises one or more polymeric components (constituents) of native ECM.

According to one non-limiting example of the ECM-derived material, ECM is isolated from a vertebrate animal, for example, from a warm blooded mammalian vertebrate animal including, but not limited to, human, monkey, pig, cow, sheep, etc. The ECM may be derived from any organ or tissue, including without limitation, urinary bladder, intestine, liver, heart, esophagus, spleen, stomach and dermis. The ECM can comprise any portion or tissue obtained from an organ, including, for example and without limitation, submucosa, epithelial basement membrane, tunica propria, etc. In one non-limiting embodiment, the ECM is isolated from urinary bladder, which may or may not include the basement membrane. In another non-limiting embodiment, the ECM includes at least a portion of the basement membrane. In certain non-limiting embodiments, the material that serves as the biological component of the scaffold consists primarily (e.g., greater than 70%, 80%, or 90%) of ECM. In another non-limiting embodiment, the biodegradable elastomeric scaffold may contain at least 50% ECM, at least 60% ECM, at least 70% ECM, and at least 80% ECM. In yet another non-limiting embodiment, the biodegradable elastomeric scaffold comprises at least 10% ECM. The ECM material may or may not retain some of the cellular elements that comprised the original tissue such as capillary endothelial cells or fibrocytes. The type of ECM used in the scaffold can vary depending on the intended cell types to be recruited during wound healing or tissue regeneration, the native tissue architecture of the tissue organ to be replaced, the availability of the tissue source of ECM, or other factors that affect the quality of the final scaffold and the possibility of manufacturing the scaffold. For example and without limitation, the ECM may contain both a basement membrane surface and a non-basement membrane surface, which would be useful for promoting the reconstruction of tissue such as the urinary bladder, esophagus, or blood vessel all of which have a basement membrane and non-basement membrane component.

Commercially available ECM preparations can also be used as the biological polymeric component of the scaffold. In one non-limiting embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton, Mass.). In another non-limiting embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

The matrix may take many different forms. In certain non-limiting embodiments, the matrix s formed as a flexible fabric that can be sewn directly on to the site to be treated, as in the abdominal wall replacement methods described herein. The matrix can be affixed in place at the site of implantation or affixed using a medically acceptable adhesive. In one non-limiting embodiment, the scaffold is substantially planar (having much greater dimension in two dimensions and a substantially smaller dimension in a third, comparable to bandages, gauze, and other substantially flexible, flat items). In another non-limiting embodiment, the matrix is tubular, and can be attached by anastamosis to tissue such as intestine or blood vessel tissue. The matrix can be electrodeposited in two or more steps, with different polymers being deposited at different locations and/or electrosprayed with different media at different times, for instance containing different growth factors, biological components, etc. to generate a 3-dimensional structure that may be used for partial or complete organ replacement.

The biodegradable elastomeric scaffold can also have three-dimensional shapes useful for treating wounds and tissue deficiencies, such as plugs, rings, wires, cylinders, tubes, or disks. A useful range of thickness for the biodegradable elastomeric scaffold is between from about 10 μm (micrometers or microns GO) to about 3.5 cm, including increments therebetween, including, without limitation from about 10 μm to about 50 μm, 50 μm to 3.5 cm, 100 μm to 3.0 cm, and between 300 μm and 2.5 cm.

In certain non-limiting embodiments, the formation and initial processing of the synthetic polymeric component and the biological polymeric component are separate. For example, the synthesis and dissolution of the synthetic polymeric component may involve solvents that would adversely affect the desirable biological properties of the biological polymeric component. By performing the synthesis and initial processing of the synthetic polymeric component separately from the corresponding synthesis and initial processing steps of the biological polymeric component, it is possible to substantially protect the biological polymeric component against degradation that it would otherwise face when exposed to the solvents used in the synthesis and processing the synthetic polymeric component. In certain non-limiting embodiments, the synthetic polymeric component and biological polymeric component are dispersed in different solvents and subsequently combined (e.g., by electrospraying the biological component onto the polymer matrix as it is being electrodeposited). For example, the electrosprayed media may comprise dissolved/solubilized collagen, elastin, ECM-derived material or other biopolymers, though concentrations or Mw of the biopolymer might need to be minimized in order to keep the electrosprayed solution viscosity within tolerances.

A poly(ester urethane) urea elastomer (PEUU) may be made from polycaprolactonediol (MW 2,000) and 1,4-diisocyanatobutane, with a diamine; such as putrescine as the chain extender. A suitable PEUU polymer may be made by a two-step polymerization process whereby polycaprolactone diol (Mw 2,000), 1,4-diisocyanatobutane, and putrescine are combined in a 1:2:1 molar ratio though virtually any molar feed ratio may suffice so long as the molar ratio of each monomer component is >0. In one embodiment, the molar feed ratio of polycaprolactone diol plus putrescine is equal to that of diisocyanatobutane. In the first polymerization step, a 15 wt % solution of 1,4-diisocyanatobutane in DMSO is stirred continuously with a 25 wt % solution of diol in DMSO. In the second step, stannous octoate is added and the mixture is allowed to react at 75° C. for 3 hours, with the addition of triethylamine to aid dissolution. A poly(ether ester urethane) urea elastomer (PEEUU) may be made by reacting polycaprolactone-b- polyethylene glycol-b-polycaprolactone triblock copolymers with 1,4-diisocyanatobutane and putrescine. In a preferred embodiment, PEEUU is obtained by a two-step reaction using a 2:1:1 reactant stoichiometry of 1,4-diisocyanatobutane:triblock copolymer:putrescine. In the first polymerization step, a 15 wt % solution of 1,4-diisocyanatobutane in DMSO is stirred continuously with a 25 wt % solution of triblock copolymer diol in DMSO. In the second step, stannous octoate is added and the mixture is allowed to react at 75° C. for 3 hours. The reaction mixture is then cooled to room temperature and allowed to continue for 18 h. The PEEUU polymer solution is then precipitated with distilled water and the wet polymer is immersed in isopropanol for 3 days to remove unreacted monomer and dried under vacuum.

Poly(ester carbonate)urethane urea (PECUU) and poly(carbonate)urethane urea (PCUU) are described, for example, in Hong et al. (Tailoring the degradation kinetics of poly(ester carbonate urethane)urea thermoplastic elastomers for tissue engineering scaffolds Biomaterials, doi: 10.1016/j.biomaterials.2010.02.005). Poly(ester carbonate urethane)urea (PECUU) is synthesized, for example using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of $Sn(Oct)_2$. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then the flask is than placed in an oil bath and kept at 70° C. overnight. The polymer is precipitated in an excess volume of cool deionized water and then dried in a vacuum at 60° C. for 3 days. The polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

The electrodeposited matrices described herein are "wet electrodeposited" meaning a liquid, such as a serum-containing liquid, is deposited as the polymer is electrodeposited. One method would be to spray the liquid onto a rotating mandrel at the same time the polymer is deposited. In one embodiment, the liquid is electrosprayed onto the matrix in substantially the same manner as the polymer is electrospun, the only difference being the deposited liquid is less viscous than the polymer, and the potential difference is such that droplets, rather than fibers are deposited. In one embodiment, the liquid is serum in normal saline, PBS, cell culture medium or a balanced salt solution, optionally comprising other additives. In the example below, the electrosprayed medium is Dulbecco's Modified Eagle Medium (DMEM) with 10% fetal bovine serum (FBS), 10% horse serum, 1% penicillin/streptomycin, and 0.5% chick embryo extract. As can be recognized by those of ordinary skill in the relevant arts, there are a multitude of salt solutions, buffered salt solutions, media, media supplements, active agents, such as antibiotics, growth factors and cytokine, biopolymers and ECM-derived material that would serve equally as a substitute for the electrosprayed serum-containing liquids described in the examples below. Compositions that are do not include blood products are referred to herein as physiological solutions, which are biocompatible, aqueous solutions, including salt solutions and blood-product-free medium, though blood products can be added to the physiological solutions. Other potentially useful media include, without limitation: DMEM, MEM, RPMI 1640, F10, OptiMEM, serum-free media, EMEM, EBM-2, F12, IMDM, and Media 199 (available, e.g., from Invitrogen). Salt solutions may be used instead of media, such as, without limitation: saline, normal saline (approximately 0.9% (w/v)), Dulbecco's phosphate-buffered salines, Hanks' balanced salt solutions, phosphate buffered salined or Earle's balanced salt solutions. Media supplements include, without limitation: HEPES, Calcium chloride, or sodium bicarbonate. Antibiotics include, without limitation: actinomycin D, ampicillin, carbenicillin, cefotaxime, fosmidomycin, gentamycin, kanmycin, neomycin, penicillin streptomycin, polymyxin B and streptomycin. Mixtures of more than one media, supplement, or antibiotic can also be used.

According to one embodiment, the electrosprayed liquid comprises one or more xenogeneic, allogeneic, isogenic, syngeneic or autologous blood products, such as serum, plasma or platelet-rich plasma. "Serum" is a cell-free, fibrinogen-free blood fraction. In one non-limiting embodiment, an aliquot of a patient's blood is removed and serum is prepared from the blood by allowing the blood to clot and removing the clotted material and cellular material, typically by first "ringing" the sample, and then by centrifugation: Plasma is made by centrifuging a tube of fresh blood containing an anti-coagulant in a centrifuge until the blood cells fall to the bottom of the tube. Platelet Rich Plasma is defined as a volume of the plasma fraction of autologous blood having a platelet concentration above baseline. (See, generally, Sampson et al. Curr Rev Musculoskelet Med. 2008 December; 1(3-4):165-74). One method of preparing platelet-rich plasma is by density-gradient centrifugation and collection of the buffy coat. A device, such as the Biomet Biologics GPS® III device can be used to obtain a platelet rich plasma fraction. Platelet-rich buffy coat preparations can be mixed with plasma, serum, saline, PBS or any suitable salt, buffer, media, etc.

Stabilizing compositions, such as stabilizing proteins may be included in the electrosprayed liquid composition. Likewise viscosity enhancers, including, without limitation: polymeric compounds may also be added.

Allogeneic blood fractions, such as one or more of serum, plasma or platelet-rich plasma, may be used. An electrospray liquid to be concurrently electrosprayed during electrodeposition of the polymer component of the matrices described herein may comprise blood fraction (e.g., serum, plasma or platelet-rich plasma, or mixtures thereof) concentrations ranging from approximately 1% to 100%, including any increment therebetween, such as 1%, 5%, 10%, 20%, 30%, 40%, 50%, 60%, 70%, 80%, 90% and 100% and any increment therebetween. In one embodiment, the electrospray liquid comprises from 5%-25% autologous or allogeneic blood product(s), and in another embodiment, 20%. When the blood fraction(s) is not 100% of the electrospray liquid, the electrospray liquid will comprise a suitable aqueous liquid, such as water, normal saline, PBS, or a cell culture medium as described above. As described elsewhere herein, the electrospray liquid also may comprise antibiotics, buffers, active agents, growth factors, cytokines, biopolymers, ECM derived material etc. in appropriate concentrations.

Because the electrodeposition/electrospinning process may be controlled either manually or by computer, different ratios of polymer and electrosprayed liquid may be deposited in different layers of the matrix. For example, the ration of liquid to polymer may increase in regions of the matrix where it is desirable to get increased cell infiltration, though too much liquid could lead to polymer delamination.

The biodegradable polymers useful herein also can be, and are preferably elastomeric. Generally, an elastomeric polymer that has properties similar to that of the soft tissue to be replaced or repaired is appropriate. For example, in certain embodiments, the polymers used to make the device is distensible. Non-limiting examples of suitable polymers include those that have a breaking strain of from 100% to 1700%, more preferably between 200% and 800%, and even more preferably between 325% and 600%. In particularly preferred embodiments, the breaking strain of the polymer is between 5% and 50%, more preferably between 10% and 40%, and even more preferably between 20% and 30%. Further, it is often useful to select polymers with tensile strengths of from 10 kPa-30 MPa, more preferably from 5-25 MPa, and even more preferably between 8 and 20 MPa. In certain embodiments, the initial modulus is between 10 kPa to 100 MPa, more preferably between 10 and 90 MPa, and even more preferably between 20 and 70 MPa.

In certain embodiments, the polymers used herein also release therapeutic agents when they degrade within the patient's body. For example, the individual building blocks of the polymers may be chosen such that the building blocks themselves provide a therapeutic benefit when released in situ through the degradation process. In one particularly preferred embodiment, one of the polymer building blocks is putrescine, which has been implicated as a substance that causes cell growth and cell differentiation.

In other embodiments, at least one therapeutic agent is added to the bioerodable matrix or fibers, for instance during electrospraying or mixed with the liquid copolymer before electrodeposition. Useful therapeutic agents include any substance that can be coated on, attached, absorbed, adsorbed, embedded or otherwise associated with the bioerodable fibers that would provide a therapeutic benefit to a patient. Therapeutic agent may be blended with the polymer while the polymer is being processed. For example, the therapeutic agent may be dissolved in a solvent (e.g., DMSO) and added to the polymer blend during processing. In another embodiment, the therapeutic agent is mixed with a carrier polymer (for example and without limitation, a polyethylene glycol hydrogel or polylactic-glycolic acid microparticles) which is subsequently processed with the elastomeric polymer. By blending the therapeutic agent with a carrier polymer or the elastomeric polymer itself, the rate of release of the therapeutic agent may be controlled by the rate of polymer degradation. In one embodiment, a bioerodable hydrogel comprising an active agent or cells is applied to the bioerodable fibers after they are applied to a surface of a tubular tissue.

Additionally, other active agents that may be incorporated into the bioerodable matrix or fibers include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, antiinflammatory cytokines, and antiinflammatory proteins or steroidal anti-inflammatory agents), antibiotics, anticlotting factors such as heparin, Pebac, enoxaprin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethasone, dexamethasone, flumethasone, isoflupredone, methylpred-nisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, becacizumab, neovastat; (3) antiproliferatives such as sirolimus, paclitaxel, perillyl alcohol, farnesyl transferase inhibitors, FPTIII, L744, antiproliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; (5) drugs acting on immunophilins, such as cyclosporine, zotarolimus, everolimus, tacrolimus and sirolimus (rapamycin), interferons, TNF binding proteins; (6) taxanes, such as paclitaxel and docetaxel; statins, such as atorvastatin, lovastatin, simvastatin, pravastatin, fluvastatin and rosuvastatin; (7) nitric oxide donors or precursors, such as, without limitation, Angeli's Salt, L-Arginine, Free Base, Diethylamine NONOate, Diethylamine NONOate/AM, Glyco-SNAP-1, Glyco-SNAP-2, (±)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (8) antibiotics, such as, without limitation: acyclovir, afloxacin, ampicillin, amphotericin B, atovaquone, azithromycin, ciprofloxacin, clarithromycin, clindamycin, clofazimine, dapsone, diclazaril, doxycycline, erythromycin, ethambutol, fluconazole, fluoroquinolones, foscarnet, ganciclovir, gentamicin, iatroconazole, isoniazid, ketoconazole, levofloxacin, lincomycin, miconazole, neomycin, norfloxacin, ofloxacin, paromomycin, penicillin, pentamidine, polymixin B, pyrazinamide, pyrimethamine, rifabutin, rifampin, sparfloxacin, streptomycin, sulfadiazine, tetracycline, tobramycin, trifluorouridine, trimethoprim sulphate, Zn-pyrithione, and silver salts such as chloride, bromide, iodide and periodate. Growth factors and/or cytokines, such as, without limitation: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Any combination of the active agents described above may be combined.

Although the matrix described herein can be implanted without cells with success, cells may be microintegrated within the bioerodable matrix or fibers using a variety of methods. For example, the matrix may be submersed in an appropriate growth medium for the cells of interest, and then directly exposed to the cells. The cells are allowed to proliferate on the surface and interstices of the matrix. The matrix is then removed from the growth medium, washed if necessary, and implanted.

In another embodiment, the cells of interest are added to the liquid that is sprayed or electrosprayed onto the bioerodable matrix while the matrix is being formed by electrospinning. This method is particularly suitable when a highly cellularized tissue engineered construct is desired. In one embodiment, pressure spraying (i.e., spraying cells from a nozzle under pressure) is used to deposit the cells. In another, the cells are electrosprayed onto the non-woven mesh during electrospinning. As described herein, electrospraying involves subjecting a cell-containing solution with an appropriate viscosity and concentration to an electric field sufficient to produce a spray of small charged droplets of solution that contain cells. As a non-limiting example, the solution comprising the cells at 10 kV is sprayed onto a target charged at −15 kV while PEUU or PEEUU is electrodeposited.

The cells that may be incorporated on or into the bioerodible matrix include stem cells, progenitor (precursor) cells, smooth muscle cells, skeletal myoblasts, myocardial cells, endothelial cells, endothelial progenitor cells, bone-marrow derived mesenchymal cells and genetically modified cells. In certain embodiments, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors (IGF), transforming growth factor-beta pleiotrophin protein, midkine protein. In one preferred embodiment, the growth factor is IGF-1.

Electrodeposition, for instance electrospinning, is used herein for depositing substantially uniform fibers onto such a surface. Electrospinning is a form of electrodeposition that permits fabrication of scaffolds that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in scaffolds with inherent anisotropy. These aligned scaffolds can influence cellular growth, morphology and ECM production. For example, Xu et al. found smooth muscle cell (SMC) alignment with poly(L-lactide-co-ε-caprolactone) fibers (Xu C. Y., et al., "Aligned biodegradable nanofibrous structure: a potential for blood vessel engineering", Biomaterials 2004 (25) 877-86.) and Lee et al. submitted aligned non-biodegradable polyurethane to mechanical stimulation and found cells cultured on aligned scaffolds produced more ECM than those on randomly organized scaffolds (Lee C. H, et al., "Nanofiber alignment and direction of mechanical strain affect the ECM production of human ACL fibroblast", Biomaterials 2005 (26) 1261-1270).

Generally, electrodeposition involves placing a polymer-containing fluid (e.g., a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrodeposition, e.g., electrospinning, the polymer-containing fluid is charged by the application of high voltage to the solution or orifice (e.g., about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (e.g., 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh (matrix) is formed on the biased target.

The properties of electrospun elastomeric matrices can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system. In one particularly preferred embodiment, the electrospinning apparatus includes an orifice biased to 12 kV, a target biased to −7 kV, and a focusing ring biased to 3 kV. Moreover, a useful orifice diameter is 0.047" (I.D.) and a useful target distance is about 23 cm. A useful range of high-voltage to be applied to a polymer suspension or melt is from 0.5-30 kV, more preferably 5-25 kV, even more preferably 10-15 kV.

Electrospinning may be performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, a mandrel may be used as a target.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component include from about 1% wt. to about 15% wt., from about 4% wt. to about 10% wt. and from about 6% wt. to about 8% wt.

In electro spinning, polymer fibers are deposited about the circumference of a mandrel and to generate a planar or substantially planar structure, the electrodeposited mat/matrix is cut substantially in the direction of the rotational axis of the mandrel, or in any manner to generate a useful topology. In use, more than one electrospun mats/matrices can be attached by any useful means, such as by "sewing" using sutures, heat annealing, chemical annealing/cross-linking, etc, though it should be recognized that the method of attaching the two or more mats/matrices would have to be strong enough for the end use, e.g., to resist rupture/herniation.

Thickness of the matrix can be controlled by either adjusting the viscosity of the polymer composition to be deposited and/or adjusting duration of the electrospinning. Use of more viscous polymer composition may result in thicker fibers, requiring less time to deposit a matrix of a desired thickness. Use of a less viscous polymer composition may result in thinner fibers, requiring increased deposition time to deposit a matrix of a desired thickness. The thickness of the matrix and fibers within the matrix affects the speed of bioerosion of the matrix. These parameters are optimized, depending on the end-use of the matrix, to achieve a desired or optimal physiological effect.

Although any form of spraying is expected to be effective, the liquid, e.g. cell growth media, may be electrosprayed. Electrospraying is done essentially concurrently with the electrodeposition of polymer fibers and is conducted in an essentially identical manner. That is, a potential is created between the liquid and the target and the liquid is drawn towards the target. Useful voltage ranges for media range from 0 kV to −10 kV for the target and from 1 kV to 20 kV for the media, and preferably from −2 kV to −6 kV for the target and from 5 kV to 10 kV for the media. Because the liquid, such as cell growth media, is less viscous that polymer solutions, the liquid is dispersed onto the target as droplets rather than as a fiber. As indicated below, the essentially concurrent spraying of the electrodeposited or electrospun matrix with fiber deposition results in a structure with significantly different physical properties as well as capacity to act as an effective implant for abdominal wall repair.

In use, the nonwoven structures described herein are surgically-implanted. Methods of implanting the materials are known in the art and are a matter of using standard surgical techniques, such as for suturing a patch in place about an abdominal wall or cardiac defect. Methods of implanting are described in the examples below. For cardiac implantation, exemplary methods are described in Fujimoto et al. (An Elastic, Biodegradable Cardiac Patch Induces Contractile Smooth Muscle An Elastic, Biodegradable Cardiac Patch Induces Contractile Smooth Muscle Infarction, *J. Am. Coll. Cardiol.* published online May 24, 2007; doi: 10.1016/j.jacc.2007.02.050). Thus, in one embodiment, a patch of the nonwoven material is sutured about an infarction on the wall of the heart.

Example 1: Morphological and Mechanical Characteristics of the Reconstructed Rat Abdominal Wall Following Use of a Wet Electrospun Biodegradable Polyurethane Elastomer Scaffold Although a variety of materials are currently used for abdominal wall repair, general complications encountered include herniation, infection, and mechanical mismatch with native tissue. An approach wherein a degradable synthetic material is ultimately replaced by tissue mechanically approximating the native state could obviate these complications. We report here on the generation of biodegradable scaffolds for abdominal wall replacement using a wet electrospinning technique in which fibers of a biodegradable elastomer, poly(ester urethane)urea (PEUU), were concurrently deposited with electrosprayed serum-based culture medium. Wet electrospun PEUU (wet ePEUU) was found to exhibit markedly different mechanical behavior and to possess an altered microstructure relative to dry processed ePEUU. In a rat model for abdominal wall replacement, wet ePEUU scaffolds (1×2.5 cm) provided a healing result that developed toward approximating physiologic mechanical behavior at 8 weeks. An extensive cellular infiltrate possessing contractile smooth muscle markers was observed together with extensive extracellular matrix (collagens, elastin) elaboration. Control implants of dry ePEUU and expanded polytetrafluoroethylene did not experience substantial cellular infiltration and did not take on the native mechanical anisotropy of the rat abdominal wall. These results illustrate the markedly different in vivo behavior observed with this newly reported wet electrospinning process, offering a potentially useful refinement of an increasingly common biomaterial processing technique.

1. Introduction

A tissue engineering approach employing an implanted degradable synthetic material designed to adequately function throughout a period of tissue ingrowth and scaffold remodeling and to result in tissues which mechanically approximate the native tissue would represent a regenerative approach likely to reduce the complications seen with current replacement materials, particularly in the application areas with higher complication rates mentioned above. Toward this end, we hypothesized that generation of an engineered tissue based upon an elastic biodegradable synthetic material, electrospun poly(ester urethane) urea (ePEUU) designed to better mimic tissue passive mechanical properties prior to implantation would result in improved outcomes in the reconstruction of the abdominal wall and other sites of fascia reconstruction (Courtney T, et al. Biomaterials 2006; 27:3631-8). A concern, however, is that cellular migration into the ePEUU might not proceed in a timely fashion (Stankus J J, et al. J Biomater Sci Polym Ed 2008; 19:635-52) and that a new processing methodology might be required to facilitate the scaffold remodeling process.

In an effort to address the limited cellular infiltration and remodeling of electrospun scaffolds that might be candidates for abdominal wall replacement, we report here on the development of a "wet" electrospinning process in which electrospun PEUU fibers were concurrently deposited onto a collection mandrel with electrosprayed serum-supplemented culture medium. Abdominal wall patches generated using both wet and the traditional "dry" electrospinning processes with PEUU were evaluated in vitro and in vivo in a rat abdominal wall replacement model with an emphasis on evaluating the cellular remodeling process and changes in tensile mechanical properties under estimated physiological stress levels were evaluated. For control purposes, ePTFE patches were implanted and similarly evaluated. The results illustrate the markedly different in vivo behavior observed with wet versus dry electrospinning, offering a potentially useful refinement of an increasingly common biomaterial processing technique.

2. Materials and Methods 2.1. Scaffold Fabrication

Poly(ester urethane) urea (PEUU) was synthesized from polycaprolactone diol (Mn=2000, Sigma), 1,4-diisocyanatobutane (Sigma) and putrescine (Sigma) according to previously described methods (Guan J, et al. J Biomed Mater Res 2002; 61:493-503, also describing physical characteristics of the product).

In further detail, PEUU and PEEUU are synthesized as follows. The molar feed ratio for preparation of PEUU was polycaprolactone:diisocyanatobutane:putrescine=1:2:1, and the molar feed ratio for synthesis of PEEUU, polycaprolactone-PEG-polycaprolactone copolymer:diisocyanatobutane:putrescine=1:2:1.

PEUU synthesis: Poly(ester urethane)urea (PEUU) was synthesized from PCL diol, and BDI using putrescine as a chain extender by a two-step solvent synthesis method. The PCL:BDI:putrescine molar ratio was defined as 1:2:1. Briefly, PCL diol were completely dissolved in DMSO in a 3-neck flask with argon protection and then BDI was added to the solution, following 4 drops of $Sn(Oct)_2$. The flask was placed in an oil bath at 70° C. After 3 h, the prepolymer solution was cooled at room temperature and then a putrescine/DMSO solution was added dropwise into the agitated solution. The final polymer solution concentration was controlled to be approximately 4% (w/v). Then the flask was placed in the oil bath and kept at 70° C. overnight. The polymer was precipitated in an excess volume of cool deionized water and then dried in a vacuum at 60° C. for 3 d. The yields of all final products were approximately 95%.

For the current study, a wet electrospun PEUU (wet ePEUU) was fabricated by a combination of electrospinning and electrospraying (Stankus J J, et al. Biomaterials 2007; 28:2738-46 and Stella J A, et al. Biomaterials 2008; 29:3228-36). Cell culture medium (Dulbecco's Modified Eagle Medium (DMEM, Invitrogen) with 10% fetal bovine serum (FBS, GIBCO), 10% horse serum (GIBCO) and 1% penicillin/streptomycin (GIBCO), and 0.5% chick embryo extract (GIBCO)) was fed by a syringe pump at 0.2 mL/min into a sterilized capillary (1.2 mm inner diameter) charged at 7 kV and suspended 4 cm above the target mandrel (6 mm diameter). Concurrently, PEUU in hexafluoroisopropanol solution (12%, w/v) was fed at 1.5 mL/h from a capillary, charged at 12 kV and perpendicularly located 20 cm from the target mandrel. The mandrel was charged at −4 kV and rotated at 250 rpm (8 cm/s tangential velocity) while translating back and forth 8 cm along the x-axis at 0.15 cm/s (FIG. 1). As a control, a dry electrospun PEUU sheet (dry ePEUU) was prepared using only polymer electrospinning (without media electrospraying) using the same parameters described above.

2.2. Animal Study

Adult female syngeneic Lewis rats (Harlan Sprague Dawley Inc.) 10-12 weeks old, weighing 200-250 g were used for the abdominal wall reconstruction procedure. Rats were anesthetized with the inhalation of 1.25-2.5% isoflurane with 100% oxygen. The abdomen was shaved and prepared with povidone-iodine solution. Procedures were performed in a sterile environment on a heating blanket. The surgical procedure was based on the method previously reported by Lai et al. (J Surg Res 2005; 127:85-92). Briefly, a skin incision along the linea alba, 3.5 cm in length, was made from 2 cm caudal of the xiphoid process. A surgical defect (1×2.5 cm) involving all of the layers of the abdominal wall including the fascia, rectus muscle, and parietal peritoneum (with the exception of the skin and subcutaneous soft tissue) was then created. This anatomic defect was then subsequently repaired by one of three types of patches selected randomly. The patches (1×2.5 cm, 400 µm thick) were sutured to the abdominal fascia by a continuous 7-0 polypropylene suture without overlap between muscles and patches in direct contact with the subcutaneous tissue and the peritoneal viscera. Skin closure was obtained over the patch by double-layer suturing. The animals were allowed to recover from anesthesia and returned to their cages. For postoperative analgesic treatment, 0.1 mg/kg of buprenorphine was administered subcutaneously 2 times per day for 3 days after surgery.

The prosthetic materials used in this study were 1) dry ePEUU, 2) wet ePEUU and 3) expanded polytetrafluoroethylene (ePTFE, Impra-Bard, Tempe, Ariz.) as a control. Laminar ePTFE prosthesis was chosen as a control in the study because a laminar prosthesis, not reticular, is ideal in the case in which the prosthesis has to be placed in direct contact with viscera (Bellon J M, et al. J Laparoendosc Adv Surg Tech A 2007; 17:160-6) Both ePEUU patches were processed to 0.4 mm in thickness, matching the ePTFE sheet thickness employed. Both ePEUU patch groups were oriented so that the circumferential direction of the mandrel was aligned with the circumferential direction of the animal and that the axial direction of the mandrel was aligned with the longitudinal axis upon their implantation.

For each group, the implanted samples were surgically retrieved at 4 and 8 weeks post-implantation (n=7 per group per time point). At retrieval, animals were euthanized by isoflurane (5%) inhalation and the abdominal wall was circumferentially incised to expose the peritoneal cavity and the repair site. Representative specimens were photographed in situ for later review and comparisons. The patches were explanted by cutting along an apron border approximately 5 mm from the original suture line. Subsequently, a 1×1 cm square shape was cut from each retrieved sample (not including the suture line) and was used for mechanical characterization of implanted materials. Thickness was measured in these retrieved samples with a dial thickness gauge (L.S. Starrett Co.). The remainder of the retrieved sample from all animals was processed for the histological examination and collagen assay.

2.3. Histology and Immunohistochemistry

Hematoxylin and eosin staining (H&E) and immunohistochemical staining were performed as previously described (Fujimoto K L, et al. J Am Coll Cardiol 2007; 49:2292-300). The samples used for histology were fixed in 4% phosphate buffered paraformaldehyde for 4 h, followed by immersion in 30% sucrose solution for at least 2 days. The samples were frozen and serially cryosectioned into 8 µm-thick specimens and processed for H&E and immunohistochemical evaluation. To assess the extracellular matrix, sections were stained with the Masson's modified IMEB trichrome stain kit (IMEB Inc.). Sections for immunohistochemistry were reacted with primary antibodies against collagen type I (monoclonal 1:100, Abcam), collagen type III (monoclonal 1:400, Abcam), and elastin (polyclonal 1:100 Abcam). A polyclonal antibody against von Willebrand factor (vWF; 1:200, Abcam) was used to identify endothelial cells. A monoclonal antibody against CD68 (1:100, AbD Serotec) was used to identify macrophages. Nuclei were stained with 4',6-diamidino-2-phenyindole, DAPI (1:10,000, Sigma). A monoclonal antibody against alpha-smooth muscle actin (αSMA; 1:200, Abcam), a monoclonal antibody against calponin (1:200, Abcam), a polyclonal antibody against SM22α (1:50, Abcam), and a monoclonal antibody against 150 kDa high molecular weight caldesmon (h-caldesmon; 1:200, Abcam) were used to identify smooth muscle cell antigens, and a monoclonal antibody against alpha sarcomeric actin (1:200, Abcam) and alpha sarcomeric actinin (1:200, Sigma) for skeletal muscle cells. Slides were examined with an Olympus IX51 microscope and images captured using DP2-BSW software (Olympus America Inc.). For each retrieved sample, 10 different microscopic fields at 400× magnification for nuclei count and 10 different fields at 100× for vWF positive structures were photographed. To determine quantity of cellular infiltration into the materials, the number of nuclei was measured using a digital image analyzer (Image J, National Institutes of Health, Bethesda, Md.). Capillaries were identified as tubular structures positively stained for vWF.

2.4. Collagen Assay

Collagen levels in retrieved patches were measured by using the Sircol collagen assay kit (Accurate Chemical and Scientific Corp.), as described previously by DuBay et al. (DuBay D A, et al. Surgery 2005; 137:463-71). The approximately 100 mg (wet weight) samples of abdominal wall patches without apron tissue were weighed and mechanically dissolved with scissors and sonicator in protease inhibitor cocktail (Sigma-Aldrich) and 0.5 M acetic acid solvent (1 mL to 100 mg wet tissue weight). The samples were then stirred overnight at 4° C. and centrifuged at 16,000×g for 60 min. Sircol dye reagent (1.0 mL) was added to 10 µl of supernatant from each sample followed by placement in a mechanical shaker at room temperature for 30 min. The samples were centrifuged at 16,000×g for 10 min and the supernatant was removed. Sodium hydroxide (0.5 M, 1:0 mL) was added to the collagen-bound dye pellet to release the bound dye into solution. Aliquots of each sample (200 µL) were transferred to the wells of a 96-well plate and the optical density was measured at 540 nm. Results were normalized as mg collagen/g wet tissue.

2.5. Biaxial Mechanical Property Measurements

Biaxial mechanical testing was performed for patches prior to implantation, for native tissues removed during the implantation procedure, and for retrieved samples at each time point (4 and 8 weeks) using a method previously described (Sacks M S. J Elasticity 2000; 61:199-246). Samples were prepared for testing through immersion into Ringer's solution (82 mM NaCl, 60 mM KCl, 2 mM $CaCl_2$, 10 mM Trizma-HCl, 10 mM Trizma-base, 11 mM dextrose) supplemented with veraparnil (0.5 mM) and ethylene glycol tetraacetic acid (EGTA, 0.5 mM) for 1 h to obtain complete muscle fiber relaxation. Samples were then trimmed to achieve 10×10 mm sections for testing. A biaxial mechanical testing approach was employed as follows. Samples were tested in physiological saline solution at room temperature using a Lagrangian membrane tension (T, force/unit length) controlled protocol designed to apply constant and equal biaxial tension to the sample up to a maximum of 200 N/m. This value was chosen based on preliminary results from our laboratory that indicated this was the maximum tension that the native tissue could reliably withstand without incurring damage. Using thin slices of polypropylene suture (Ethicon) affixed to the sample to form four small markers of w1 mm in diameter in the central region used to compute local strains as well as the deformation gradient tensor F. From F, the axial stretches $\lambda_{CD}=F_{11}$ and $\lambda_{LD}=F_{22}$ were determined (CD=circumferential direction, LD=longitudinal direction). Two equi-biaxial tension protocols containing 10 cycles each were performed. The first protocol was used to precondition the sample; data were recorded from the final cycle of the second protocol. Post-processing was performed using a preconditioned free-float reference state image.

2.6. Statistical Analysis

Statistical evaluation was performed using Prism version 4.0c (GraphPad Software Inc.). Results are listed as mean±standard error of the mean. One-way analysis of variance (ANOVA) followed by Tukey-Kramer multiple comparison testing was applied where multiple comparisons were made. The Mann-Whitney U test was used for the comparison of vWF positive structures count among the wet group since these data were not normally distributed. Statistical analysis for mechanical characterization was performed by using one-way ANOVA to compare the maximum stretches observed in each sample. Differences were considered to be statistically significant at $p<0.05$.

3. Results 3.1. Material Characteristics

Wet PEUU sheet microstructure prepared using the electrospinning/electrospray method is seen in FIG. 1, as is the dry PEUU sheet. Macroscopically the wet PEUU was moist upon cutting and clearly retained culture medium within the scaffold interstices. While both dry and wet PEUU microstructures exhibited continuous polymer fibers without bead formation, the wet PEUU fibers qualitatively exhibited a greater degree of looping and more tortuosity. These structural features were consistently observed across the scaffolds generated. The average diameter of wet PEUU fibers (1549±270 nm) was found to be larger than that for dry PEUU fibers (824±47 nm) ($p<0.05$).

3.2. Postoperative Course and Gross Observations

Figure 2:
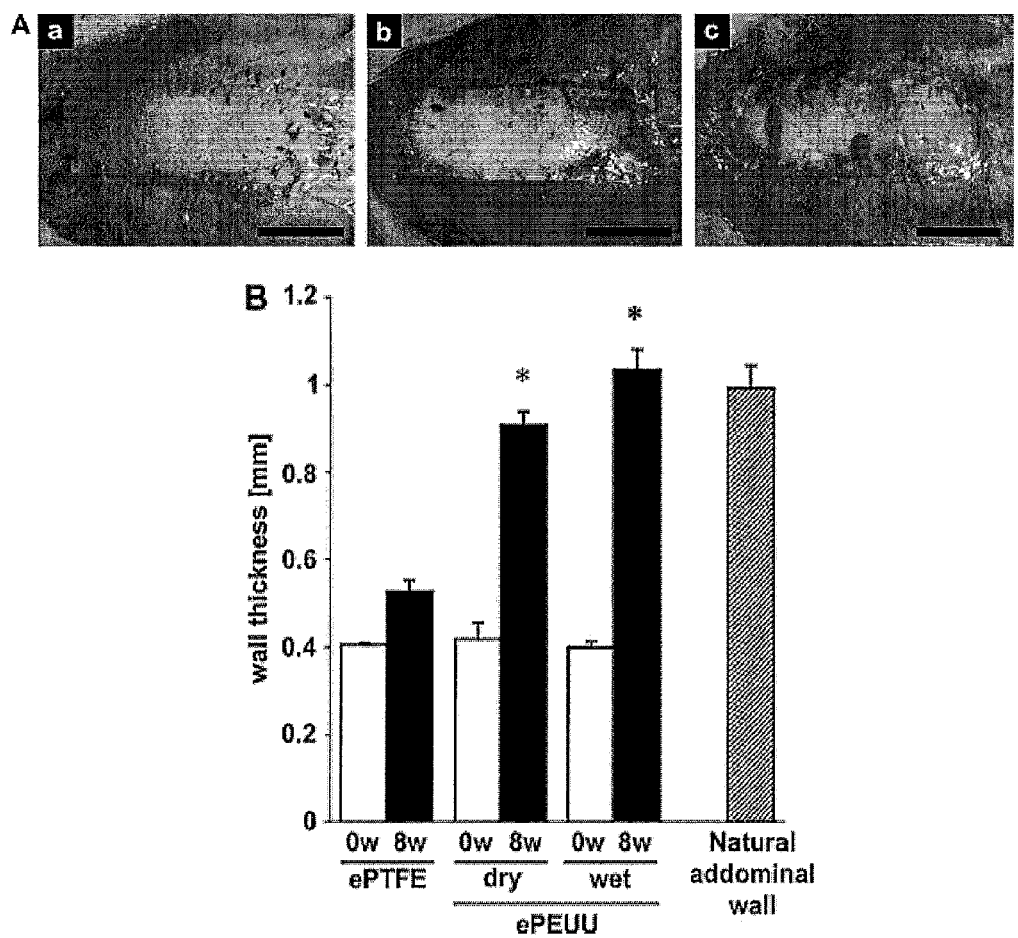
FIG. 2. (A) Macroscopic appearance of implanted ePTFE (a) dry ePEUU (b) and wet ePEUU (c) 8 weeks after surgical implantation. Scale bar: 10 mm (B) Wall thickness of patches prior to implant and after 8 weeks in vivo, as well as thickness of the native rat abdominal wall. *p<0.01 compared with ePTFE group at same time point.

No abnormal behavior indicating pain or distress, or abnormal weight gain or loss was observed after surgery. No herniation at the repair site of the abdominal wall was observed in any of the rats during the study (FIG. 2A, a-c). Additionally, no group showed any adhesions to the visceral organs at the site of the implanted patch except for slight omental tissue adhesion which was seen consistently across groups. Although the pre-implantation materials were 400 µm thick, both wet and dry ePEUU patched areas were 0.9-1 mm thick at 8 week, almost the same as native rat abdominal wall, while ePTFE showed no apparent change in thickness (FIG. 2B). Considering that the thickness measured includes the thickness of neoperitoneum formed, this result suggests that neo-formation of tissue beneath and above ePTFE was minimal.

3.3. Histology and Immunochemistry 3.3.1. H&E and Masson's Trichrome Staining

Figure 3:
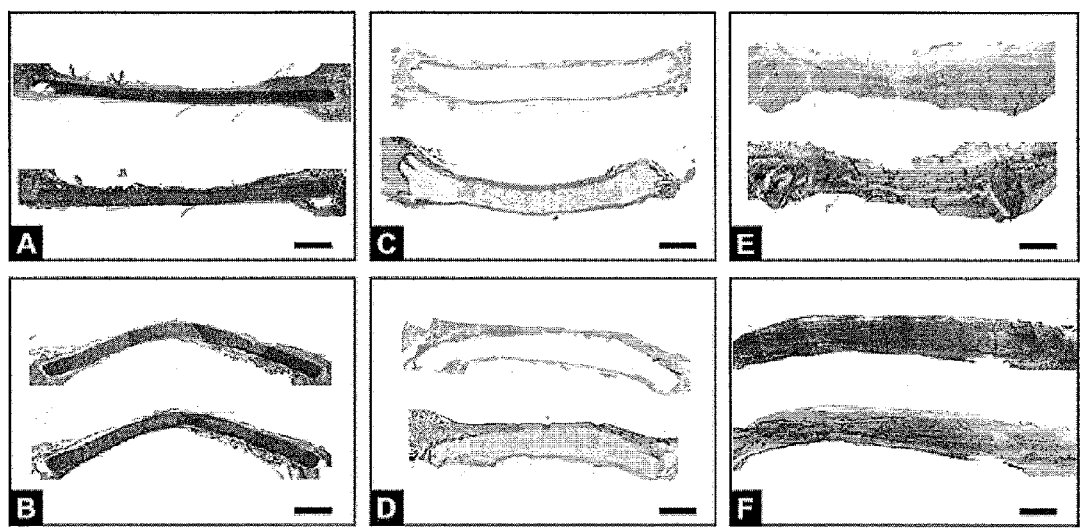
FIG. 3. Representative cross-section mosaic images of implanted ePTFE (A and B), dry ePEUU (C and D), and wet ePEUU (E and F). The upper row is from 4 week explants (A, C, and E) and the lower row from 8 week explants (B, D, and F). Within each box, staining for the upper image is with H&E, and for the lower image with Masson's trichrome. Scale bar: 1 mm.

Under light microscopy, all of the prosthetic materials showed layered fibrous tissue surrounding the materials at each time point (FIG. 3). Almost no tissue ingrowth was observed in ePTFE, while for wet ePEUU polymer degradation was accompanied by collagenous fiber deposition. Collagenous fiber deposition indicated by blue staining in the Masson's trichrome images of FIG. 3, increased at the 8 week time point in the interior of the wet ePEUU, whereas no staining suggestive of collagenous deposition was seen within the dry ePEUU patches.

3.3.2. Cellular Infiltration

Figure 4:
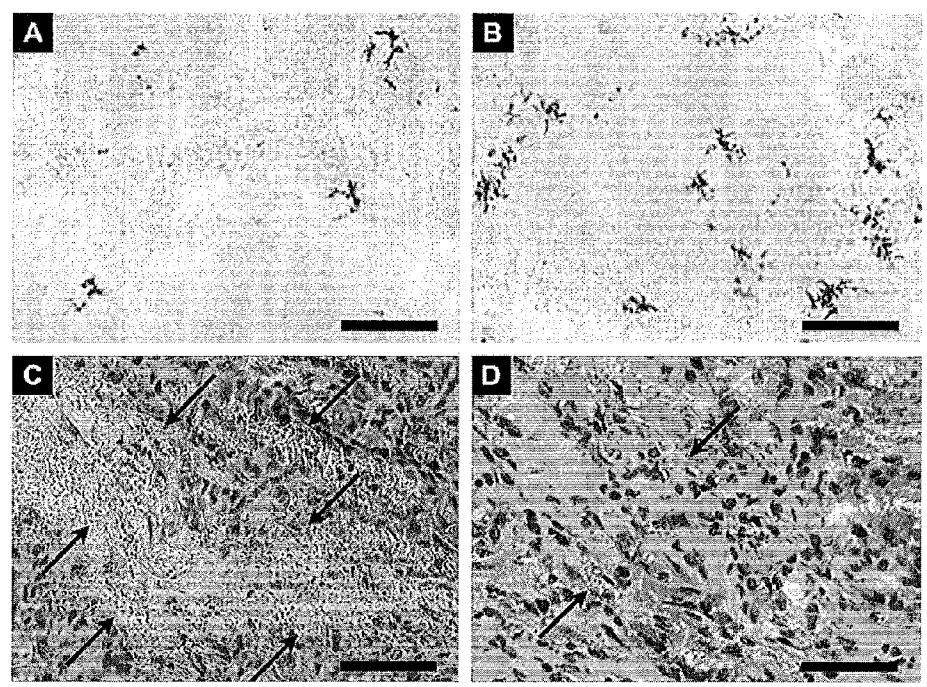
FIG. 4. High magnification micrographs of dry ePEUU with H&E staining for 4 (A) and 8 (B) week explanted specimens, as well as wet ePEUU explanted patches at 4 (C) and 8 (D) weeks. Arrows in wet ePEUU micrographs indicate remnant ePEUU in the specimen. Scale bar: 50 μm.
Figures 1, 5:
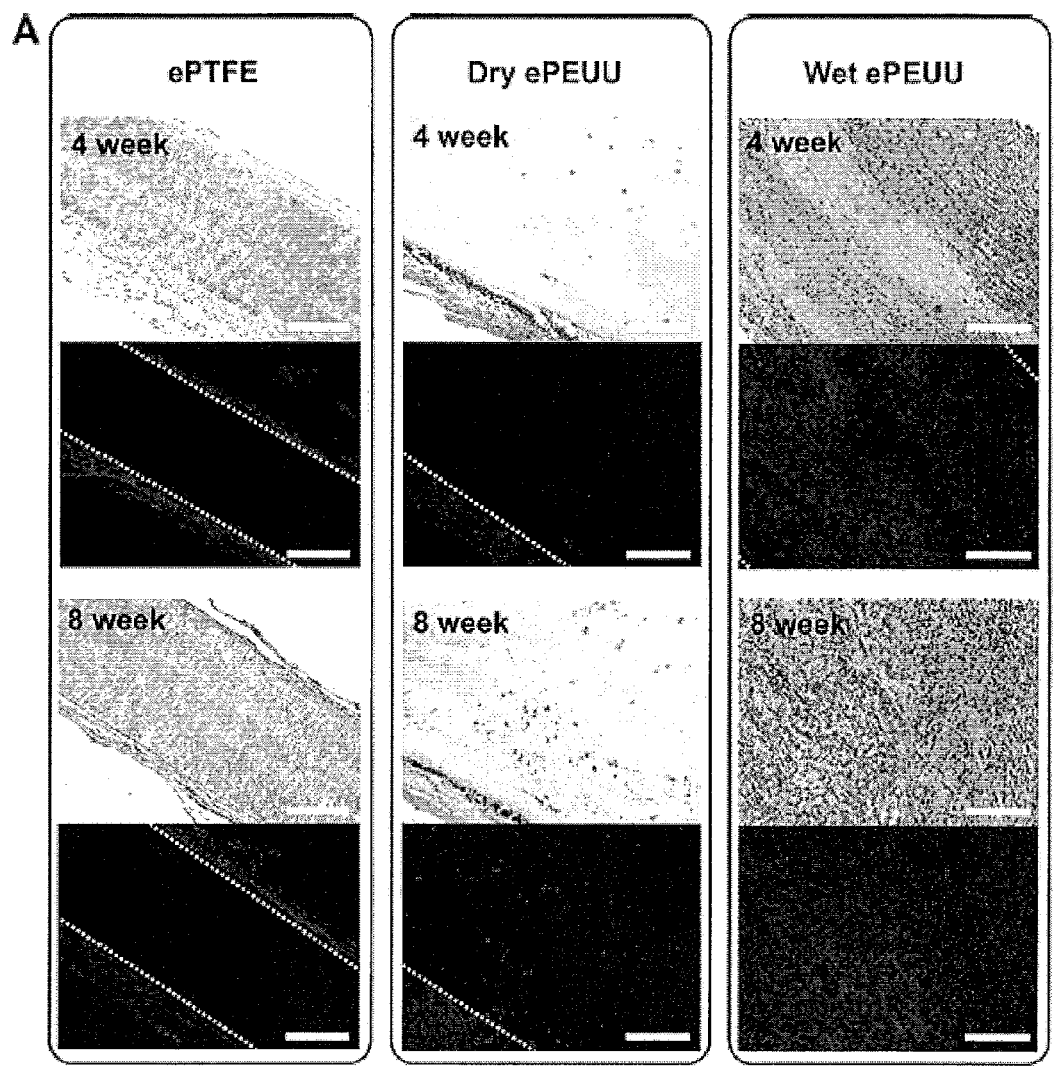
FIG. 5. (A) Hematoxylin and eosin (H&E) and nuclear staining for each implanted material at each time point. (B) Quantification of nuclei as a measure of cellular infiltration. Scale bar: 200 mm *p<0.01 compared with both ePTFE group and dry ePEUU group at each time point.
Figures 2, 5:
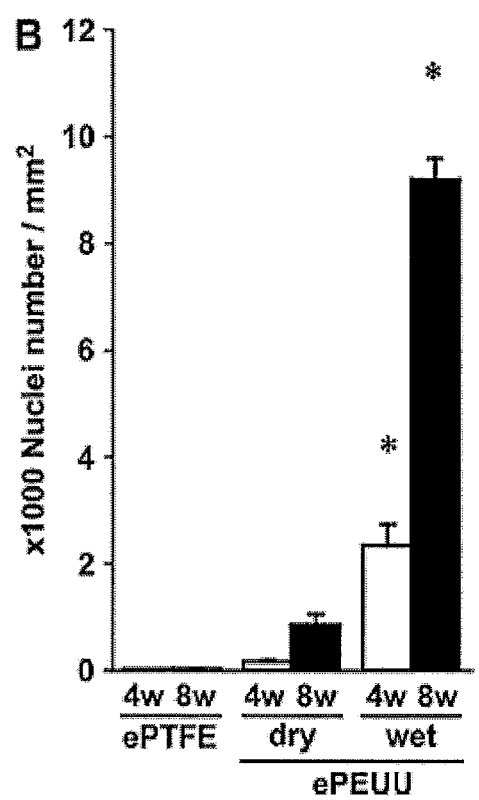
Figure 6:
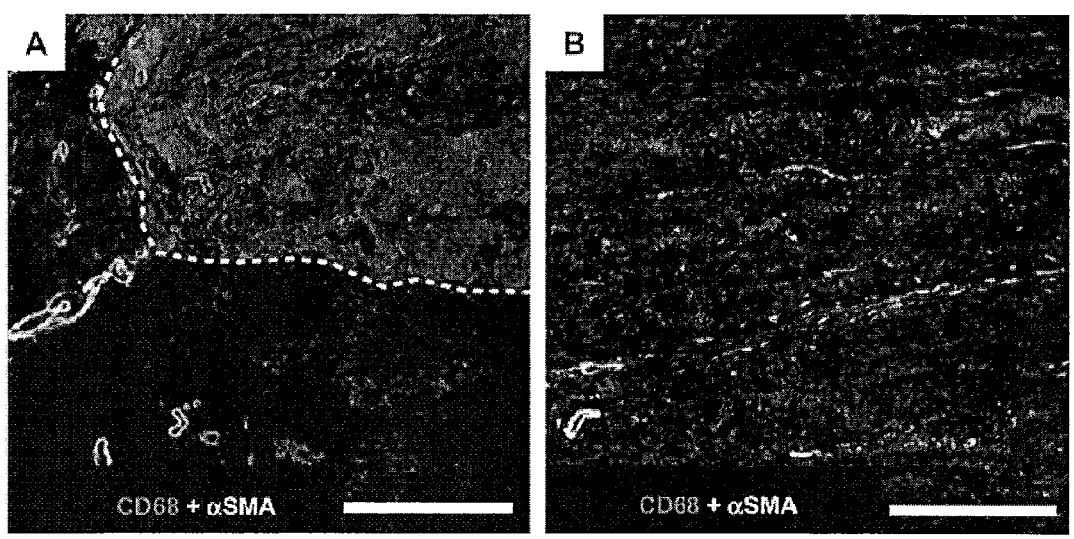
FIG. 6. Immunostaining for CD68 and α-smooth muscle actin for wet ePEUU patches explanted after 8 weeks. Nuclear staining is blue, α-smooth muscle actin is green, and anti-CD68 for macrophage labeling is red. (A) At the edge of the patch, the boundary between the implanted material and native abdominal wall is indicated with white broken line. (B) Inner portion of the wet ePEUU. Scale bar=100 μm.

High magnifications of dry and wet ePEUU H&E stained sections at 4 and 8 weeks point are shown in FIG. 4. In dry ePEUU some positive labeling is detected that may represent a sparse cellular infiltrate into the polymer matrix. In contrast, wet ePEUU exhibited substantial cellular migration near the center of the patch at 4 weeks surrounding the remaining ePEUU fibers. By 8 weeks this infiltration is largely complete although regions of fibers are still clearly visible. For a more specific evaluation of cellular infiltration FIG. 5 shows nuclear staining of sections from the three patch types at the two explant times and quantification of nuclear numbers. Virtually no cellular infiltration was noted in the ePTFE patches at either time. Modest cellular infiltration occurred in the dry ePEUU group by 8 weeks. For the wet ePEUU cell numbers were significantly increased compared to the dry group at both 4 and 8 week time points. Immunostaining for CD68 in wet ePEUU patches at 8 weeks revealed macrophage infiltration into the wet ePEUU, that was more predominant in the edge regions and lighter in the central areas (FIG. 6).

3.3.3. Neovascularization

Figures 1, 7:
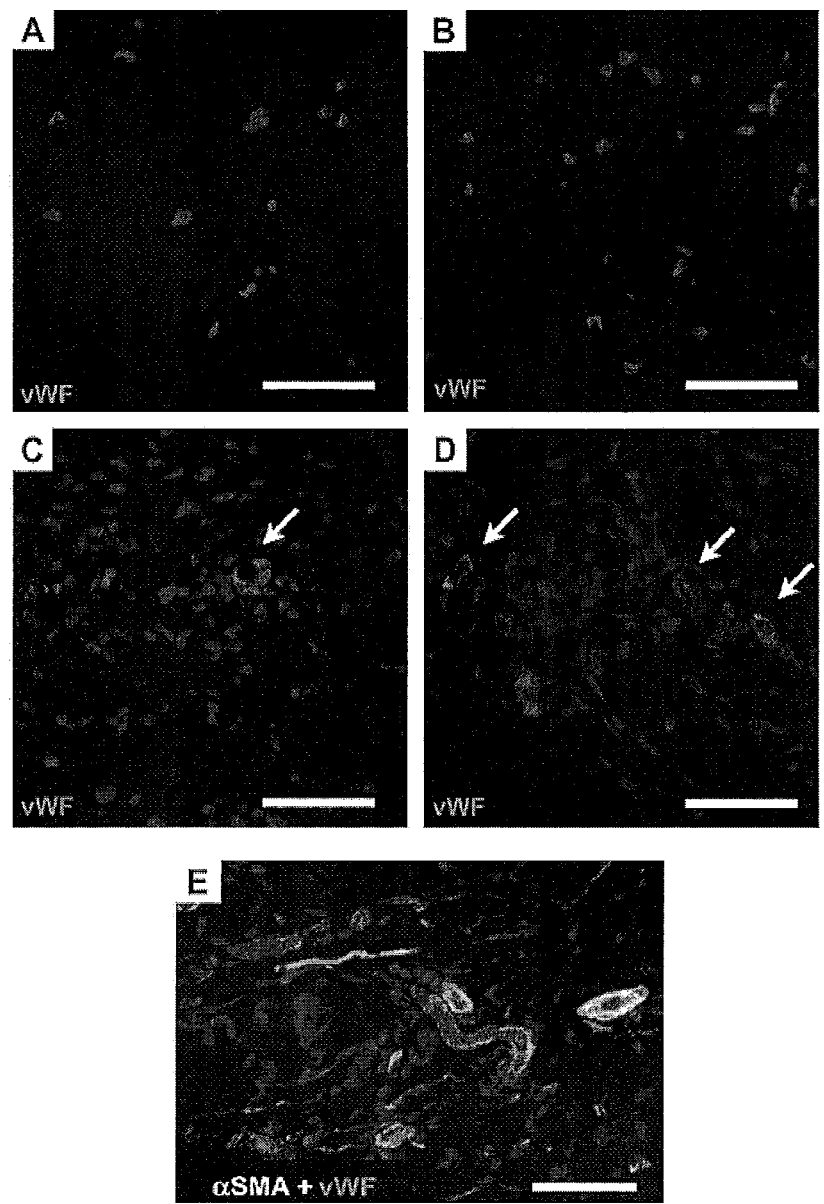
FIG. 7. Immunohistochemical staining for vWF in dry ePEUU explanted patches at 4 (A) and 8 weeks (B), and wet ePEUU at 4 (C) and 8 weeks (D). With double staining, vWF(+) structures (red) are seen to be surrounded by α-smooth muscle actin positive cells (green, E), implying vascular ducts. Quantification of vWF labeled structures is summarized in (F). Scale bar: 50 μm. *p<0.05 compared with dry ePEUU group at 8 week point.
Figures 2, 7:
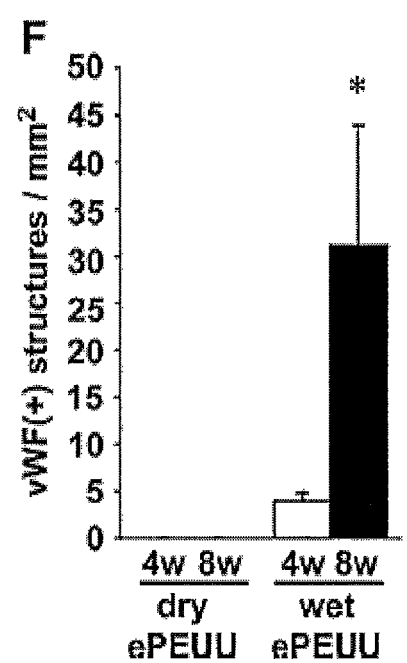

The vascular density within the patches, as assessed by vWF immunostaining, is seen in FIG. 7. No positive staining was seen for either the ePTFE or dry ePEUU at any time point, whereas the wet ePEUU patches demonstrated sparse vWF positive structures at 4 weeks, and significantly increased numbers of such structures at 8 weeks ($p<0.05$). In many instances these vWF positive structures were found to be surrounded by α-smooth muscle actin positive cells (FIG. 7E) suggesting the presence of smooth muscle cells. The spatial relationship in the double positive staining with vWF and αSMA suggest mature vascular formation (Bir S C, et al. J Vasc Surg 2009; 50:870-9).

3.3.4. Extracellular Matrix Deposition

Figure 8:
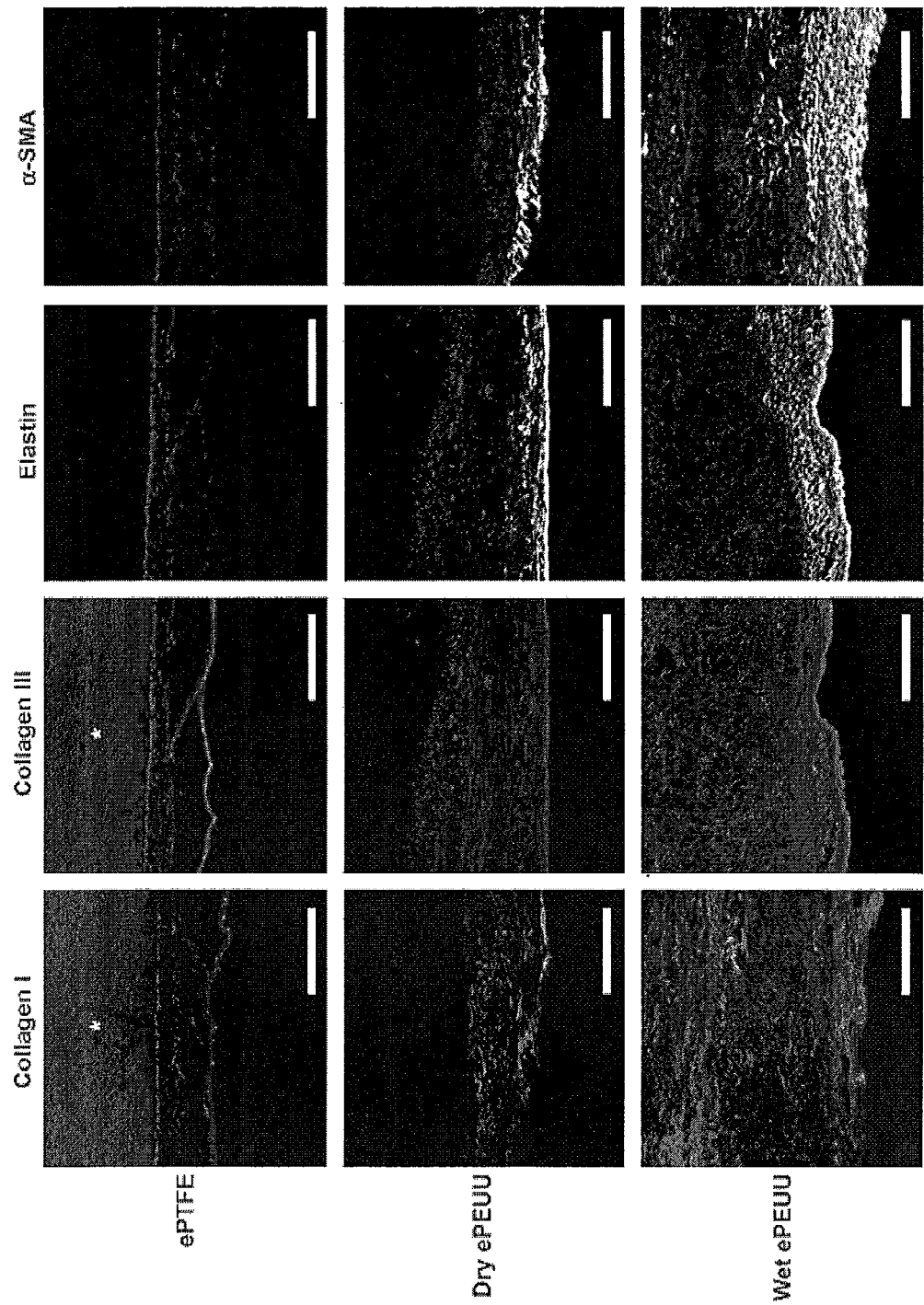
FIG. 8. Immunostaining for collagen type I, collagen type III, elastin, and α-smooth muscle actin of ePTFE, dry ePEUU, and wet ePEUU explanted patches 8 weeks after implantation. * on ePTFE micrographs indicates nonspecific antibody binding. Scale bar: 100 μm.
Figure 9:
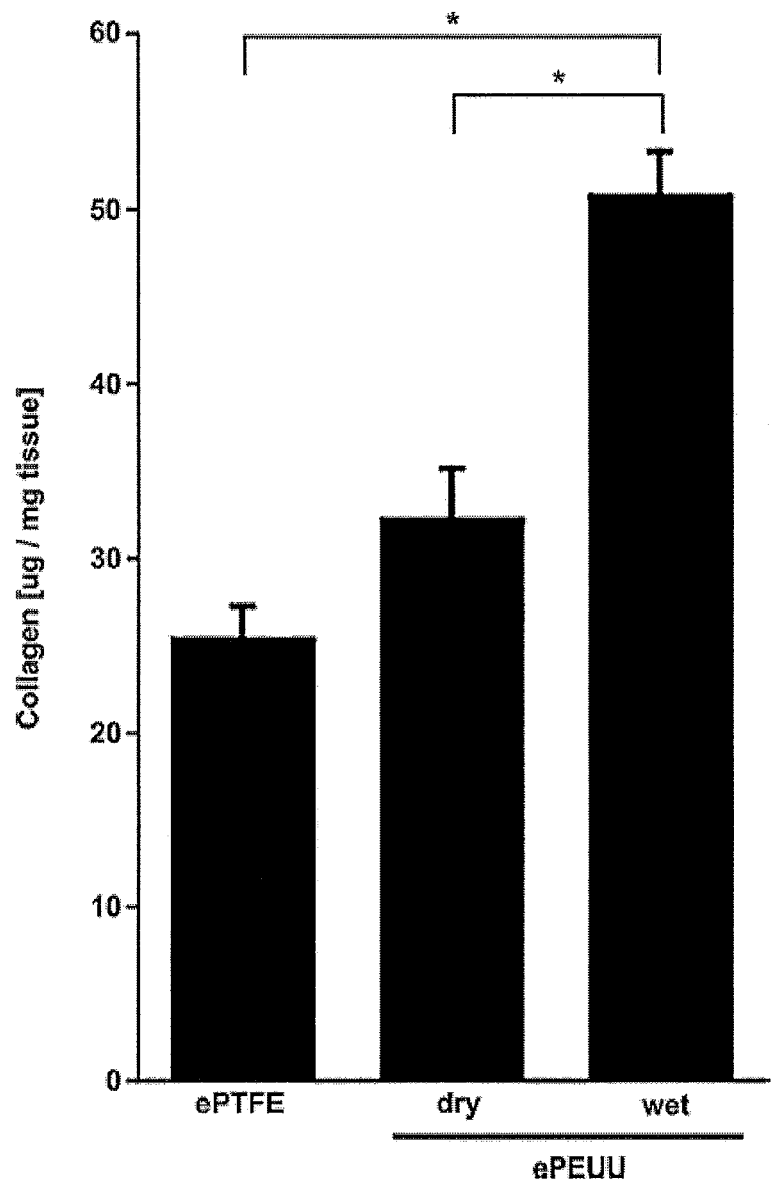
FIG. 9. Collagen protein concentration in explanted abdominal patch region at 8 weeks, standardized by tissue wet weight. *p<0.05.
Figure 10:
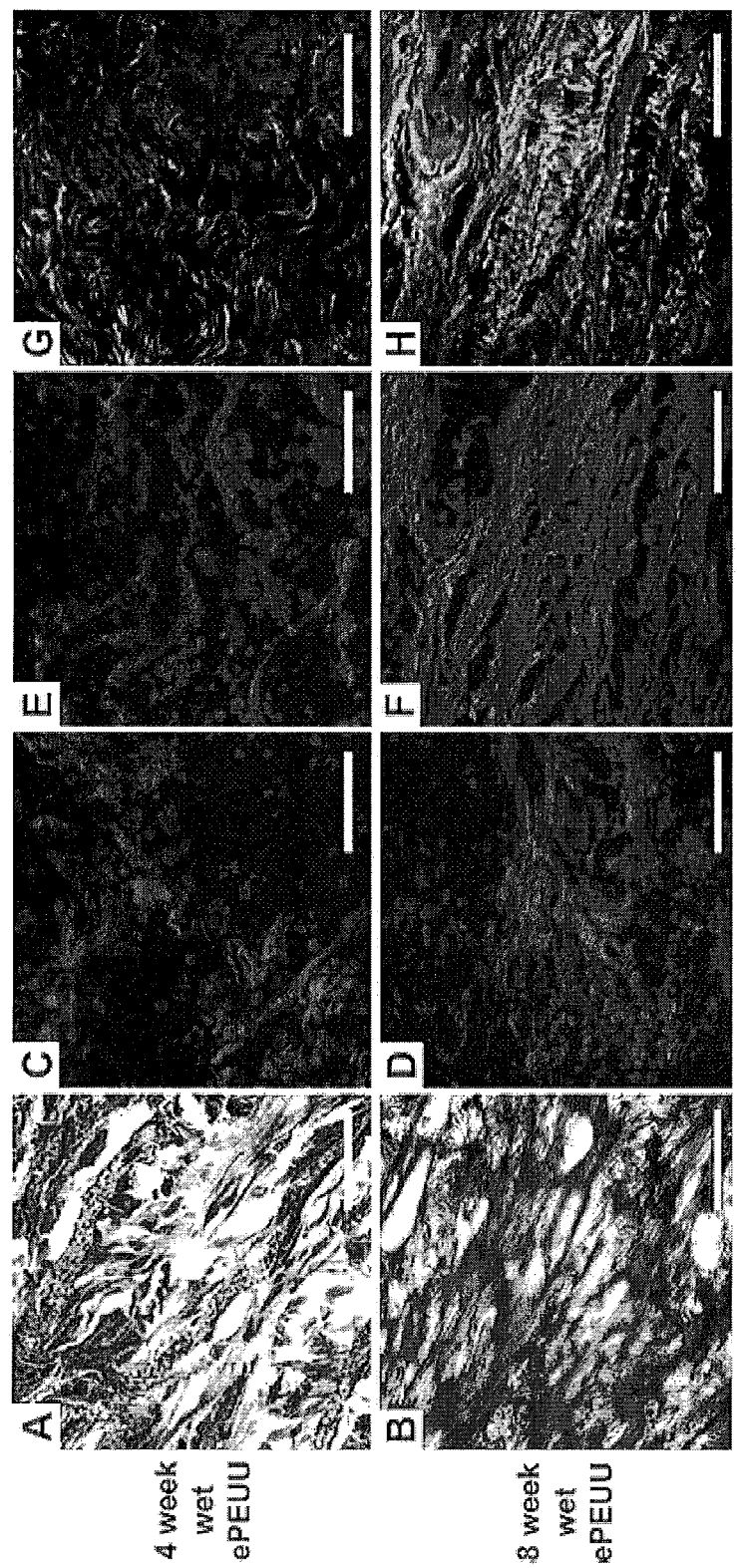
FIG. 10. High magnifications of wet ePEUU Masson's trichrome staining at 4 (A) and 8 (B) week time point, collagen type I (C and D), collagen type III (E and F), and elastin (G and H). Scale bar: 50 μm.

Immunostaining against collagen types I and III, and elastin at 8 weeks revealed substantial extracellular matrix (ECM) component elaboration within wet ePEUU patches, but minimal such deposition in dry ePEUU patches and none within ePTFE (FIG. 8) consistent with the cellular infiltration findings. All three materials had substantial ECM deposition onto the patch exterior surfaces. With dry ePEUU the ECM deposition within the patch was associated with the cellular infiltrate near the surfaces. Inside the wet ePEUU substantial deposition of types I and III collagen was observed. The collagen assay, performed on the patches including the surface ECM deposition, showed significantly greater collagen levels from the wet ePEUU patches than for the other two patch types at 8 weeks (FIG. 9). Histologically examining the wet ePEUU patch at 4 versus 8 weeks a trend could be qualitatively appreciated in ECM deposition increasing with time (FIG. 10).

3.3.5. Immunostaining for Muscle Cell Markers

Figure 11:
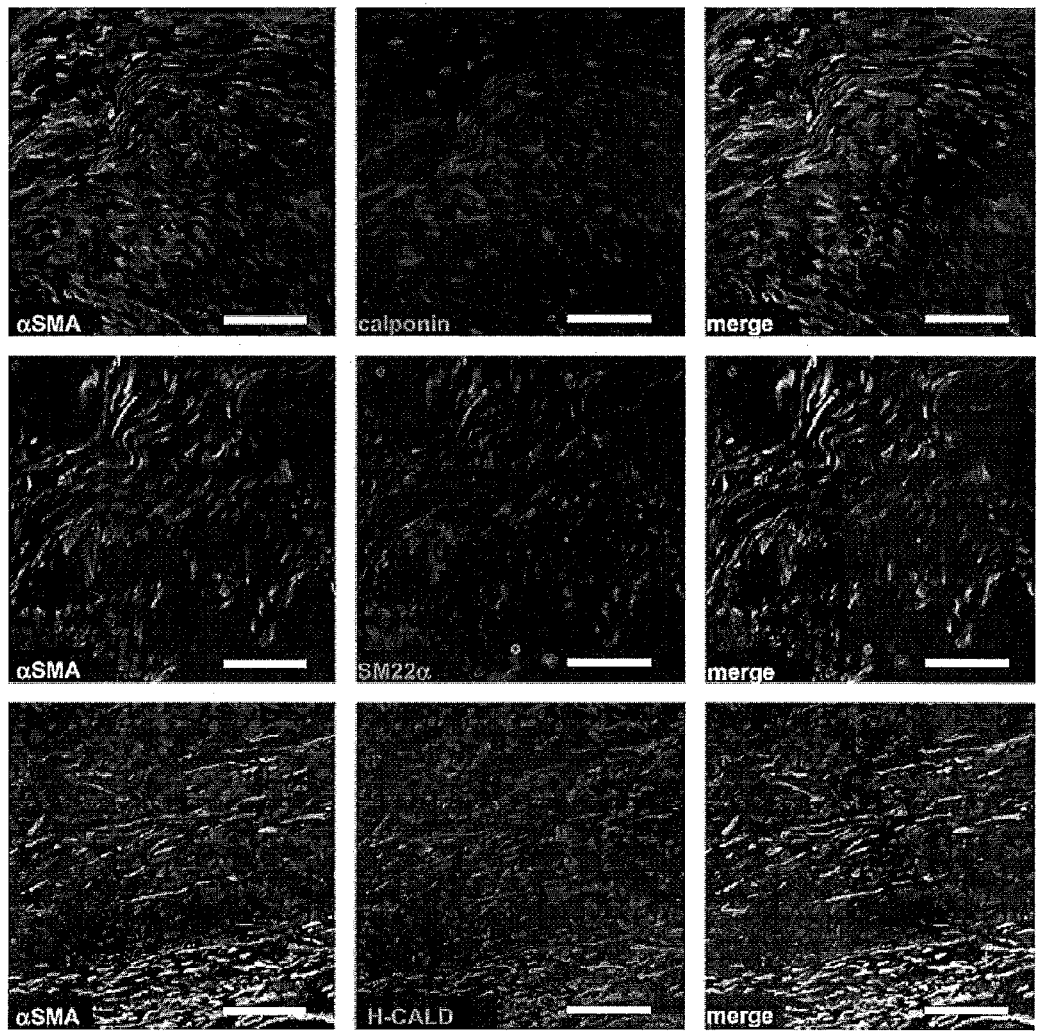
FIG. 11. Immunostaining for αSMA, calponin, SM22α, and h-caldesmon in 8 week wet ePEUU patches. αSMA (+) cells co-localize with calponin, SM22α, and h-caldesmon. Scale bar: 50 μm.

The cellular infiltrate in the 8 week wet ePEUU patches was also evaluated in terms of immunostaining for muscle cell markers. Skeletal muscle markers including alpha sarcomeric actin and alpha sarcomeric actinin were not found in the examined sections. However, alpha-smooth muscle actin positive cells were found on the surfaces of both ePEUU patch types and in the cellular infiltrate for the wet ePEUU patches. In evaluating the presence of contractile markers for smooth muscle cells, immunostaining for smooth muscle cell specific antigen calponin was positive for both wet and dry ePEUU patch surfaces. For the cellular infiltrate in wet ePEUU, calponin, SM22α, and h-caldesmon were all evident (FIG. 11). The relative degree of staining for each antigen (−=not present; +=present; ++=strongly present) is presented in Table 1.

TABLE 1

Relative degree of immunohistochemical labeling of cells associated with implanted patches.

|  |  | αSMA | calponin | SM22α | HCALD | α-actinin | α-actin |
|---|---|---|---|---|---|---|---|
| ePTFE | surface | − | − | − | − | NA | NA |
|  | inner | − | − | − | − | NA | NA |
| dry ePEUU | surface | + | + | − | − | NA | NA |
|  | inner | − | − | − | − | NA | NA |
| wet ePEUU | surface | ++ | ++ | ++ | ++ | − | − |
|  | inner | + | + | + | + | − | − |

Figures 1, 12:
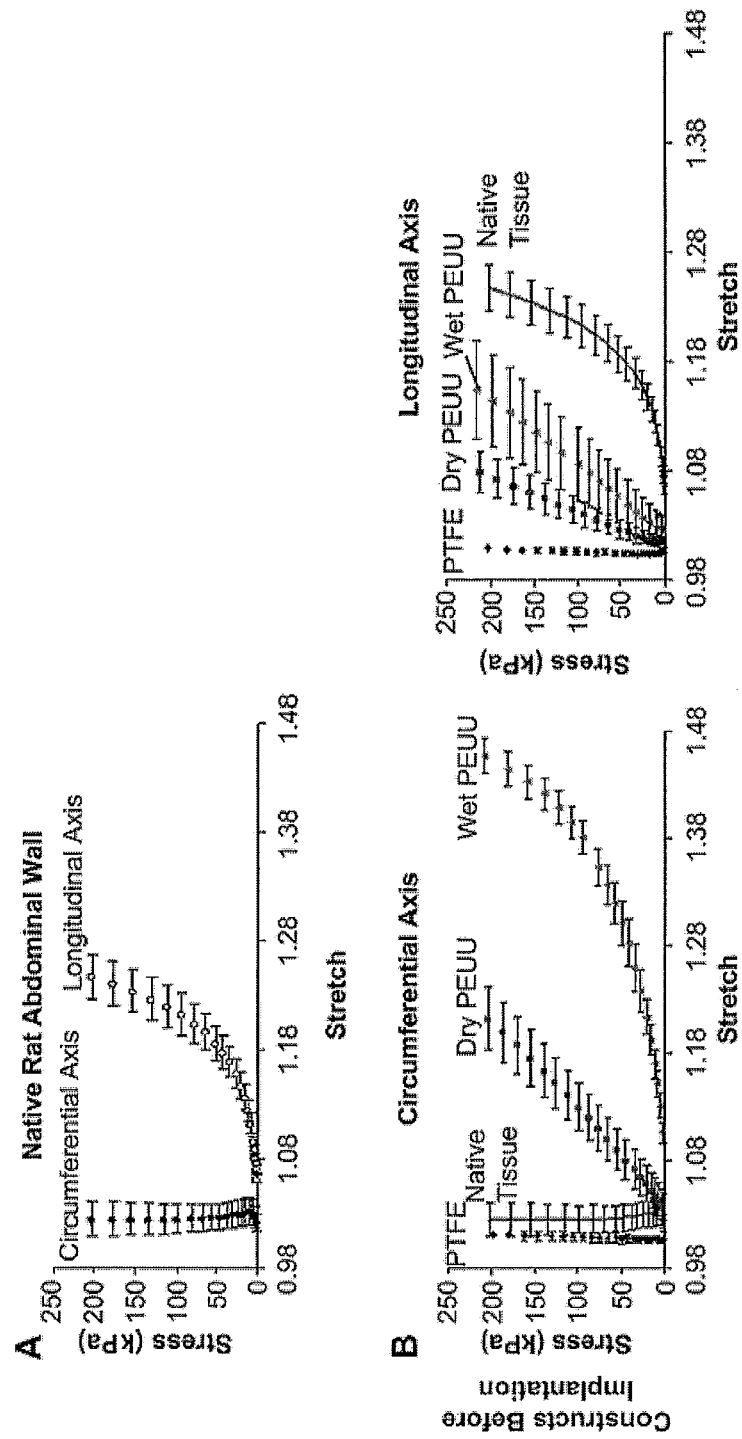
FIG. 12. Biaxial stress-stretch curves of native abdominal wall tissue (A) and for patch materials 4 and 8 weeks post-implant (B). Under equal planar biaxial tension, normal abdominal wall tissue exhibits a high degree of anisotropy, with the circumferential axis being markedly stiffer than the longitudinal axis. Wet ePEUU remodels in vivo to approach this pattern at 8 weeks to a much greater degree than the controls.
Figures 2, 12:
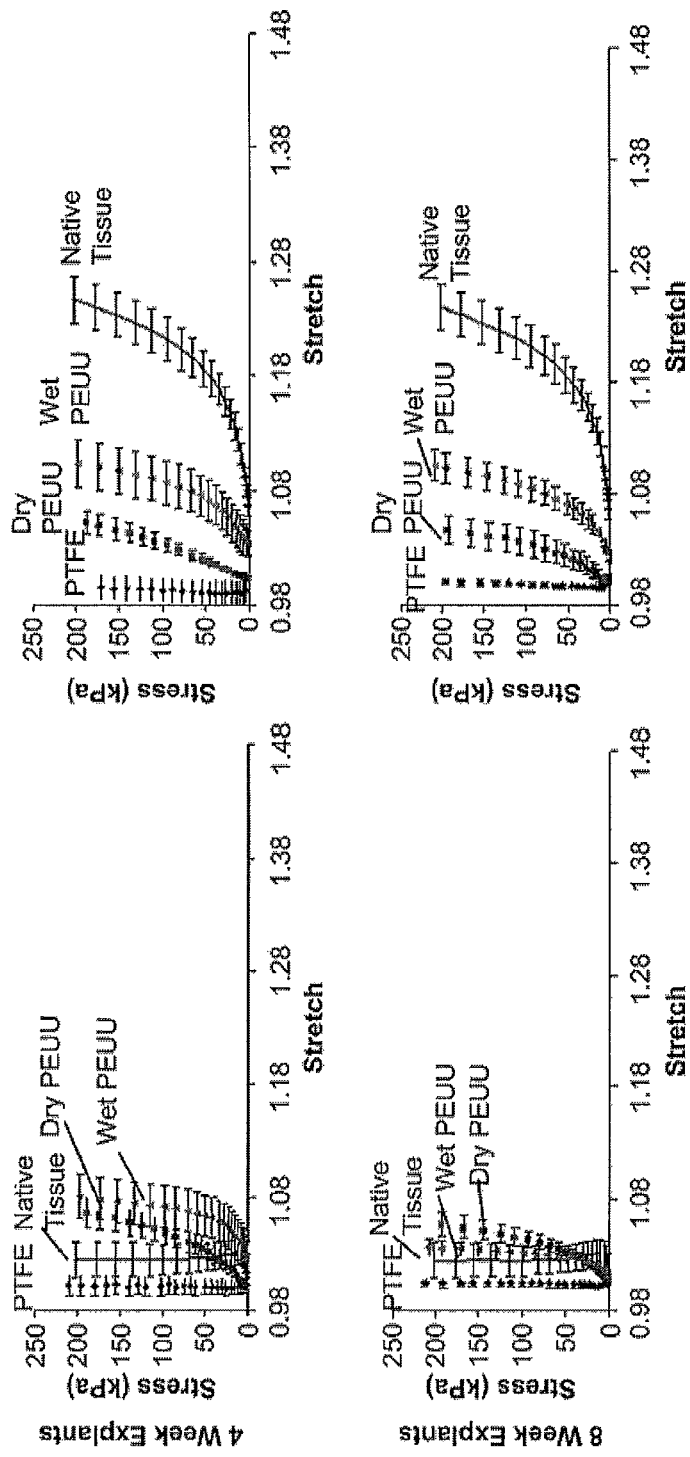

− = not present;
+ = present;
++ = strongly present;
NA = not assessed 3.4. Biaxial Mechanical Property Measurements Native rat abdominal wall tissue was found to possess a very high degree of anisotropy upon applied equal planar biaxial tension with the circumferential axis being markedly stiffer than the longitudinal axis ($p<0.0001$; FIG. 12A). Prior to implantation, each patch material exhibited distinct mechanical properties. The ePTFE patch material was largely isotropic, and very stiff, deforming less than 5% in either direction under the maximum applied tension (FIG. 12B). In contrast, dry ePEUU was significantly more compliant in the circumferential axis ($p<0.001$). The addition of sterile media to the ePEUU construct during fabrication of wet ePEUU served to make both axes more compliant ($p<0.05$). Compared to the native tissue, the circumferential axis was again significantly more compliant ($p<0.001$). It was also found that, before implantation, the ePEUU constructs both displayed an anisotropy ($p<0.01$) that was stiffer in the longitudinal (axial) direction relative to the circumferential direction, in contrast to the native tissue. Following an implantation period of four weeks, a marked difference can be seen in the mechanical properties of the elastomeric constructs (FIG. 12B). Both dry and wet ePEUU became markedly stiffer and more isotropic ($p<0.05$). Wet ePEUU remained more compliant than dry ($p<0.05$), but only in the longitudinal axis. The ePTFE showed no change and was again the most stiff and isotropic. After 8 weeks, wet ePEUU exhibited a reversal from the implanted anisotropy to exhibit a mechanical behavior that more resembled native tissue ($p<0.001$ for 4 versus 8 weeks and for longitudinal versus circumferential direction at maximum stretch levels). Neither dry ePEUU nor ePTFE groups changed significantly between four and eight weeks of implantation.

4. Discussion

When repairing large abdominal wall defects, applying simple surgical closure may lead to increased abdominal pressure and adversely affect visceral function through the development of abdominal compartment syndrome (ACS). In trauma patients, injury itself may lead to ACS, which is treated with damage control laparotomy to relieve pressure at the expense of an open abdominal wound. This laparotomy wound is reduced mechanically with time, but will ultimately still require permanent abdominal wall reconstruction in the majority of cases. Prosthetic materials are required to allow repair of abdominal defects to avoid ACS as well as to avoid hernia recurrence. Desirable abdominal wall prostheses properties include infection resistance, elasticity and strength, acceptably low foreign body effect, and facilitation of vascularized tissue ingrowth without induction of bowel adhesions. Currently there are no materials that completely address all of these concerns.

The role of biomaterial mechanical properties in abdominal wall repair is well recognized in a general sense, with weak materials being associated with a risk for herniation and materials that are too stiff being associated with patient discomfort. The degree to which these factors come into consideration varies with the extent of the repair being considered. Abdominal wall compliance after prosthesis implantation was shown in a small animal study to be the most important mechanical property for predicting a low incisional hernia recurrence rate (DuBay D A, et al. Surgery 2006; 140:14-24). Incisional hernia repair, which may be associated with increased stiffness in the abdominal wall, potentially due to fibrosis and atrophy, results in a progressive mechanical impedance mismatch that increases the transfer of load forces to the wound healing interface and increases herniation risk. Moreover, preservation of elasticity would also allow the abdominal wall to function more naturally in a dynamic fashion, maintaining its flexibility and avoiding abdominal stiffness and sites of compliance mismatch. It then follows that special consideration should be given to the compliance of biomaterials chosen for this application.

Here, novel prosthetic materials possessing varied tensile properties and microstructures were implanted into an abdominal wall defect model with particular attention to materials that might better mimic the native tissue behavior.

Mechanical characteristics of these implanted elastomeric constructs changed substantially during the implantation period. This change can be explained through the ingrowth of host tissue into the construct matrix as well as implanted material degradation. As ePTFE has been shown to be absent of tissue ingrowth, it follows that its properties would remain largely unchanged throughout the course of implantation, as was observed. FIGS. 3-5, 8 and 9 show the cellular infiltration and ECM elaboration within the constructs, and the relatively small quantity of biological material found within dry ePEUU at the time of explant. This modest deposition may explain the moderate stiffening effect observed for the dry ePEUU. For wet ePEUU, the collagen assay and histological results suggested that more extensive changes in the mechanical results might be expected given the level of cellular ingrowth which is concomitant with the macrophage infiltration and ECM elaboration observed. At four weeks, collagen and elastin were shown to be present, but were disorganized. By eight weeks, the elaborated ECM and cellular components had become more extensive, serving as the likely factor producing the change in anisotropy from what was observed at implantation to an anisotropy which mimicked native tissue. It is important to note that the suture line was not included in the sections that were mechanically tested. This was done to ensure a proper representation of the explant mechanical properties, rather than suture strength. Gross examination of the explanted tissue, as well as the lack of herniation in any animal indicated that breaks at the anastomosis did not occur.

In considering a biodegradable material approach to abdominal wall replacement, the most obvious risk is that the material will lose strength before sufficient tissue ingrowth and organization has occurred, thus putting the site of repair at risk for failure. As discussed above, in the case of dry ePEUU, the degradation of mechanical properties did not appear to be an issue in the period of study, and for ePTFE this is not a concern for the material. For wet ePEUU we were interested in the nature of the ingrowing tissue, both mechanically and in terms of the cellular and ECM constituency. If the scaffold were to be replaced by other than thin and stiff fibrotic scar tissue, this might ultimately be an improved functional result for the patient in terms of passive mechanical properties. Both the wet and dry ePEUU implants varied from ePTFE in terms of the surface tissue that surrounded the scaffolds, with αSMA and calponin positive cells being found. The wet ePEUU material further varied from dry ePEUU in that these near surface cells were also positive for contractile smooth muscle cell markers SM22α and h-caldesmon. In addition, the extensive cellular infiltrate in the wet ePEUU consistently stained positive for the array of contractile smooth muscle cell markers examined by immunohistochemistry. Stressed myofibroblasts could generate collagen fibers and have actin filaments as a contractile element, however, D'Addario et al. reported that h-caldesmon in particular is a specific marker of fully differentiated smooth muscle (D'Addario S F, et al. J Cutan Pathol 2002; 29:426-9). In other work with PEUU scaffolds we have observed the contractile phenotype of smooth muscle cells, confirmed with immunohistochemical staining as well as electron microscopy, in the area near degraded PEUU scaffolds placed on cardiac tissue (Fujimoto K L, et al. J Am Coll Cardiol 2007; 49:2292-300). The passive mechanical properties of this biological material replacing the scaffold appeared to better mimic native tissue, although clearly more temporally extended studies would be needed to examine the ultimate outcome of the scaffold remodeling process in both wet and dry ePEUU implants. The active functionality of any smooth muscle tissue is also unclear. For this report the tissue was clearly not organized sufficiently to merit such an evaluation. Whether this nascent tissue might ultimately develop into organized structures with active mechanical properties is also not clear, although the goal of this replacement approach currently is to achieve improved passive mechanical properties.

From a materials processing perspective, a major aspect of this investigation was the comparison of traditional dry electrospinning versus the wet technique wherein cell culture medium is electrosprayed concurrently with electrospun fiber deposition. We have previously reported a technique wherein cells in culture medium are electrosprayed concurrently with PEUU electrospinning to form a tissue construct that has cells integrated on a microscale within it (Stankus J J, et al. Biomaterials 2007; 28:2738-46 and Stankus J J, et al. Biomaterials 2006; 27:735-44). The technique of this example is in a sense a derivative of that technique with the difference being that here cells are not utilized. We hypothesized that the so-called wet electrospinning technique with culture medium would lead to improved cellular migration since serum factors would be deposited throughout the scaffold forming process and in early control experiments we qualitatively noticed that wet electrospinning resulted in scaffolds with softer mechanical properties and a distinct morphology with more fiber tortuosity (looping) that might putatively ease cell migration by more readily locally distended fibers. It was also considered that the wet electrospinning process might lead to less inter-fiber bonding, which would also ease cell migration and contribute to scaffold softening. Quite recently there has been a brief report in the literature (Yokoyama Y, et al. Mater Lett 2009; 63:754-6) where another "wet" electrospinning technique was used. In that method, electrospun fibers were directly deposited onto fluid surfaces of varying surface tension to form scaffolds of increased porosity, and as in our method, apparently increased fiber tortuosity. For the present study, the specific mechanisms by which wet electrospinning would allow cell migration were not the focus, rather we sought to investigate whether this process might indeed result in a different scaffold remodeling result in an application of clinical relevance, abdominal wall repair. As mentioned above, in this application area a regenerative approach that results in a more physiological result mechanically would be attractive.

The findings of slow cellular infiltration into dry ePEUU were expected. In subcutaneous implantations comparing dry ePEUU with dry ePEUU blended to a varying degree with a urinary bladder derived ECM, we found little degradation of dry ePEUU, presumably due to both slow polymer hydrolysis and the lack of macrophage access to interior fibers due to the tight fiber format (Stankus J J, et al. J Biomater Sci Polym Ed 2008; 19:635-52). With ECM blended scaffolds, degradation was markedly accelerated, attributed to increased fiber degradation due to the protein blending (Stankus J J, et al. J Biomater Sci Polym Ed 2008; 19:635-52; El-Kurdi M S, et al. Biomaterials 2008; 29:3213-20; and Sell S A, et al. Adv Drug Deliv Rev 2009; 61:1007-19) and thus increased cellular access. With wet ePEUU processing protein was not incorporated per se into the fibers, although serum proteins would have likely adsorbed in the process. These serum factors may have served to encourage cellular infiltration, and with macrophages, possibly increased phagocytic activity. It was also observed that fiber diameter was increased for wet ePEUU. This may have been due to the deposition process leading to less dense fibers that are not pulled to the same extent from adhesion point to adhesion point as in dry electrospinning, due to fiber-fiber sliding in the wet environment. Such loosely deposited fibers might be less dense or less crystalline and might hydrolyze more rapidly, but we did not specifically investigate these potential effects. To separate scaffold morphology effects from culture medium deposition effects, a follow up investigation comparing wet ePEUU formed by electrospraying with a buffered salt solution to electrospraying with culture medium would be of interest.

For clinical application one might wish to consider the use of an allogenic serum solution possibly supplemented with ionic species, should these prove to be determinant in achieving a required morphology. The use of serum in this process, with its array of growth factors and adhesion molecules, would be attractive versus isolated growth factors (as is done for controlled release applications) and specific adhesion molecules from both an economic and regulatory perspective. The general approach of using wet electrospinning to create an elastic scaffold incorporating a growth factor rich protein solution may find application in other clinical areas. Repair of the pelvic floor and fascial replacement in a variety of other settings such as breast, oral and maxillofacial reconstructive surgery might benefit from such soft constructs (Natale F, et al. Curr Opin Urol 2006; 16:407-12 and Sergent F, et al. Eur J Obstet Gynecol Reprod Biol 2009; 147:106-1) and postmastectomy reconstruction (Becker S, et al. Plast Reconstr Surg 2009; 123:1-6).

Several limitations of the current report should be mentioned. First, the scaffold remodeling process and mechanical property changes were only observed over an 8-week period. Although the wet ePEUU had substantially degraded during this period, the sustainability of the developing architecture for longer periods is not clear. Future studies in a larger animal model with longer time points would better define the clinical potential of this approach. A larger animal model would also allow the evaluation of more appropriately sized implants and would better mimic the physical forces experienced by the human abdomen, although quadrupeds remain limited for this purpose.

5. Conclusions

A new wet electrospinning technique in which biodegradable elastomer fibers were concurrently deposited with electrosprayed culture medium was found to result in markedly different scaffold mechanical behavior and to experience much greater cellular infiltration and scaffold remodeling in vivo versus dry electrospun constructs. In a model for abdominal wall replacement in the rat, wet ePEUU scaffolds provided a healing result that better approximated physiologic passive mechanical behavior and where an extensive cellular infiltrate possessing contractile smooth muscle markers was observed together with extensive ECM elaboration, Control implants of dry ePEUU and ePTFE did not experience substantial cellular infiltration and did not take on the native mechanical anisotropy of the rat abdominal wall.

Example 2: Preparation of an Autogenic Rat Abdominal Wall Repair Matrix

Whole rat blood is obtained from syngeneic rats. Rat serum is prepared from the whole blood by allowing the blood to clot, and then removing the clot by ringing and centrifugation. Platelet rich plasma is prepared as described above. Multiple samples of PEUU and PEEUU polymer are electrospun onto a mandrel concurrently with electrospraying of various dilutions of rat serum or platelet rich plasma in normal saline and PBS to final serum or platelet rich plasma concentrations of 0%, 10%, 20%, 50%, 75% and 100% (v/v), essentially as described in Example 1. Each wet-electrospun matrix is removed from the mandrel by cutting the matrix along its long axis.

The resultant 11 matrices (0%, 10%, 20%, 50%, 75% rat serum or platelet rich plasma in normal saline, 0%, 10%, 20%, 50%, 75% rat serum or platelet rich plasma in PBS and 100% rat serum or platelet rich plasma) are implanted in separate, syngeneic rat abdominal walls as described in Example 1. The rats are sacrificed at 8 weeks to determine the level of cell infiltration and tissue regeneration as described in Example 1.

Example 3—Human Abdominal Wall Repair

Human serum or platelet rich plasma is obtained according to standard practice substantially as described in Example 2. The serum or platelet rich plasma is diluted in normal saline to a final concentration of approximately one of 10%, 20%, 50%, 75%. A matrix is prepared as described in the previous examples by electrospraying 100% human serum or platelet rich plasma or 0%, 10%, 20%, 50% or 75% (v/v) human serum or platelet rich plasma in normal saline, essentially as described above. The resultant matrix is implanted in the abdominal wall of a human patient in need thereof, and remains in the patient until it dissolves. Biopsies of the implant are taken at 8 and 16 weeks post-implantation for analysis.

Example 4—Human Abdominal Wall Repair

Serum or platelet rich plasma is obtained from a patient in need of abdominal wall repair, according to standard practice substantially as described in Example 2 and above. The serum or platelet rich plasma is diluted in normal saline to a final concentration of approximately one of 10%, 20%, 50%, 75% (v/v). A matrix is prepared as described in the previous examples by electrospraying 100% human serum or platelet rich plasma or 0%, 10%, 20%, 50% or 75% human serum or platelet rich plasma in normal saline, essentially as described above. The resultant matrix is implanted in the abdominal wall of the patient in need thereof, and remains in the patient until it dissolves. Biopsies of the implant are taken at 8 and 16 weeks post-implantation for analysis.

Example 5—Human Organ Repair

Human serum or platelet rich plasma is obtained according to standard practice substantially as described in Examples 2-4. The serum or platelet rich plasma is diluted in normal saline to a final concentration of approximately one of 10%, 20%, 50%, 75% (v/v). A matrix is prepared as described in the previous examples by electrospraying 100% human serum or platelet rich plasma or 0%, 10%, 20%, 50% or 75% human serum or platelet rich plasma in normal saline, essentially as described above, optionally omitting cutting the matrix off of the mandrel in favor of sliding the matrix off of the mandrel. The resultant matrix is implanted in one of the skin, blood vessel(s), muscle, esophagus, trachea, stomach, intestine, rectum or bladder of the patient to repair damage or a defect at the site of implantation and remains in the patient until it dissolves. The serum or platelet rich plasma is obtained from the patient or one or more other humans. Biopsies of the implant are taken at 8 and 16 weeks post implantation for analysis.

Example 6—Preparation of Infarcted Model in Rats and Evaluation of Patch Materials All experimental rats (young female Lewis rats (10-week old)) undergo cardiac muscle infarction. The rats are anesthetized with isoflurane (5.0% induction and 1.25 to 1.5% maintenance with 100% oxygen). The rats undergo endotracheal intubation and are mechanically ventilated with a small animal respirator at a frequency of 60-70/min. Tidal volume is set to 0.6-2.0 ml depending on body weight of the rat. The rats are placed on a warming pad (37° C.) in the supine position. The hair on the anterior chest is trimmed with an electric clipper. The skin leads of electrocardiography are attached on both forelimbs and on the left hind limb, and the electrocardiogram is monitored. Before skin incision, one dose of lidocaine (100 mg/kg) anti-arrhythmia and cefuroxime (100 mg/kg) antibiotic is administered intramuscularly for prophylaxis of fatal arrhythmia (left ventricular fibrillation) after infarction and surgical site infection, respectively.

The skin of the left chest is sterilized with povidone-iodine solution. The surgeries are performed using aseptic techniques with sterile instruments. The rat heart is exposed through a left thoracotomy ($4^{th}$ inter-costal). After identifying the left anterior branch of rat coronary artery, it is carefully ligated with 7-0 prolene suture. If significant arrhythmia is noted on ECG monitoring, the procedure is held until the rhythm is normalized. The muscle layer and skin is then closed with 4-0 polyglactin absorbable suture (VICRYL, Ethicon, Inc.). The rats are observed in the surgical suite until fully recovered from the anesthesia, and then returned to the housing facility. The first 3 days after surgery, Tramadol (5 mg/kg) analgesia is administered 2 times a day intramuscularly, and cefuroxime (100 mg/kg) antibiotic is injected intramuscularly once a day. If the animal develops severe cardiac failure during or after the procedure, it is immediately euthanized.

The creation of infarction might cause fatal arrhythmias. Lidocaine (100 mg/kg) is administered for prophylactic therapy. These episodes are treated with cardiac compression (squeezing the heart gently by forceps when a ventricular fibrillation (VF) happens during open chest. When a VF happens after closing the chest, pressing the closed chest wall is performed soon after mechanical ventilation with 100% oxygen. The frequency is 200 times/min.

Experimental group selection: Two weeks following ligation of the coronary artery, patch implantation surgery is performed. Before surgery, animals are screened by echocardiography for infarct size as estimated by the percentage of scar area (akinetic or dyskinetic regions) to LV free wall (LVFW) area Animals with infarcts greater than 25% of the LVFW are chosen. The rest, with infarcts less than 25%, are sacrificed. After this selection, all experimental animals are divided into 5 groups:

I) Rats implanted with PEUU-PRP patches
II) Rats implanted with control electrospun PEUU patches (dry PEUU)
III) Rats implanted with control electrospun PEUU+PBS patches
IV) Rats implanted with control electrospun PEUU+cell culture media patches
V) Rats infarcted (no implantation) as a control.

Patch material is sterilized by exposure to the ultraviolet light source in a laminar flow hood (Class II A/B3 Biological Safety Cabinet) for 2 hours. The skin of the left chest of anesthesized rats (as above) is sterilized with povidone-iodine solution. The rat heart is exposed through a left thoracotomy. The infarcted part of rat cardiac muscle is readily identified because of its color. Covering the infarcted part with material, the cardiac patch is sutured using 7-0 polypropylene with over-and-over sutures. The wound is closed as above. For the sham (infarction control, group V)) surgery, the rats are anesthesized as above and the skin of the left chest is sterilized with povidone-iodine solution. The rat heart is exposed through a left thoracotomy. After observation of the infarct area, no surgical intervention is performed. The wound is closed as described above.

For hemodynamic assessment (Simultaneous Tail-cuff blood pressure measurement and Echocardiography and Pressure-volume loop measurement), rats are anesthesized as described above. Once the plane of anesthesia is established, the animal is placed in a spine position in a custom warmed glass chamber, which includes a vertical trough. Once it has been affirmed that the animal is secured and breathing adequately, the chest is shaved and prepared for echocardiographic examination. Combined blood pressure measurement (tail-cuff blood pressure system) and echocardiography are used to take measurements of left ventricular dimensions and heart inlet and out let blood flow velocities. The probe of the echocardiography machine is put on the chest wall, and ultrasonic beam detects the heart motion. This scanning is not invasive. Hemodynamic measurement is performed at 2 week after 1st surgery (creation of LV infarction) for experimental group selection, and 4 and 8 weeks after 2nd surgery.

For pressure-volume loop measurement, each animal is placed in a supine position under anesthesia at the endpoint (just before the euthanasia). The right carotid artery is exposed through small skin incision, and a catheter for real-time pressure-volume measurement (SPR-838, Millar) is inserted from the right carotid artery to left ventricle of the heart. When the measurement is done, the animal is euthanized immediately by potassium solution injection.

Having described this invention above, it will be understood to those of ordinary skill in the art that the same can be performed within a wide and equivalent range of conditions, formulations and other parameters without affecting the scope of the invention or any embodiment thereof.

We claim:

1. A method of repairing damaged or defective abdominal wall tissue in a mammal, comprising:
    implanting in the abdominal wall of the mammal at the site of the damaged or defective tissue a cell-free matrix comprising:
    a biodegradable elastomeric polymer, comprising one or both of a poly(ester carbonate)urethane urea (PECUU) and a poly(carbonate)urethane urea (PCUU), electrodeposited concurrently with a sprayed or electrosprayed liquid that comprises a cell-free mammalian blood product that is allogeneic to the mammal,
    thereby resulting in infiltration and growth of skeletal muscle cells, and mature vascular formation in the matrix, and thereby repairing the damaged or defective abdominal wall tissue.

2. The method of claim 1, in which the liquid comprises one or more of serum, plasma and platelet rich plasma.

3. The method of claim 1, in which the mammal is a human.

4. The method of claim 1, in which the sprayed or electrosprayed liquid comprises from 1% to 100% v/v of a mammalian blood product.

5. The method of claim 1, in which the sprayed or electrosprayed liquid comprises 100% serum, plasma or platelet rich plasma.

6. The method of claim 1, in which the sprayed or electrosprayed liquid comprises from 10% to 30% v/v serum, plasma or platelet rich plasma.

7. The method of claim 1, in which the sprayed or electrosprayed liquid comprises 20% v/v serum, plasma or platelet rich plasma.

8. The method of claim 1, in which the sprayed or electrosprayed liquid comprises fetal bovine serum and horse serum and optionally chick embryo extract.

9. The method of claim 1, in which the sprayed or electrosprayed liquid comprises a platelet rich plasma.

10. The method of claim 1, in which the matrix is electrospun.

11. The method of claim 1, in which the implant is implanted in the abdominal wall of the mammal, thereby repairing a defect in the abdominal wall of the mammal.

12. The method of claim 1, wherein the polymer further comprises collagen.

13. The method of claim 1, wherein the polymer further comprises elastin.

14. The method of claim 1, wherein the polymer further comprises collagen and elastin.

15. The method of claim 1, wherein the polymer comprises PCUU.

16. The method of claim 1, wherein the polymer comprises PECUU.

17. The method of claim 1, wherein the cell-free matrix further comprises at least one active agent selected from the group consisting of anti-inflammatories, immunosuppressants, antiangiogenic compositions, antiproliferative compositions, antibodies, compositions that act on immunophilins, taxanes, nitric oxide donors, antibiotics, growth factors, and combinations thereof.

18. A method of making a cell-free implantable matrix for muscle repair, comprising electrodepositing one or both of a poly(ester carbonate)urethane urea (PECUU) and a poly(carbonate)urethane urea (PCUU) and concurrently electrospraying a liquid comprising a cell-free mammalian blood product onto the electrodeposited polymer.

19. The method of claim 18, wherein the PCUU comprises poly(1,6-hexamethylene carbonate).

20. The method of claim 19, wherein a molar ratio of PCL:PHC is 75:25, 50:50, or 25:75.

21. The method of claim 18, wherein the PECUU comprises polycaprolactone (PCL) and poly(1,6-hexamethylene carbonate) (PHC).

* * * * *